(12) United States Patent
Ohashi et al.

(10) Patent No.: US 10,991,871 B2
(45) Date of Patent: Apr. 27, 2021

(54) PIEZOELECTRIC ELEMENT, PIEZOELECTRIC ACTUATOR, ULTRASONIC PROBE, ULTRASONIC DEVICE, ELECTRONIC APPARATUS, LIQUID JET HEAD, AND LIQUID JET DEVICE

(71) Applicant: Seiko Epson Corporation, Tokyo (JP)

(72) Inventors: Koji Ohashi, Matsumoto (JP); Chikara Kojima, Matsumoto (JP)

(73) Assignee: Seiko Epson Corporation

(*) Notice: Subject to any disclaimer, the term of this patent is extended or adjusted under 35 U.S.C. 154(b) by 327 days.

(21) Appl. No.: 15/718,639

(22) Filed: Sep. 28, 2017

(65) Prior Publication Data

US 2018/0090666 A1 Mar. 29, 2018

(30) Foreign Application Priority Data

Sep. 29, 2016 (JP) .............................. JP2016-191743

(51) Int. Cl.
*H01L 41/04* (2006.01)
*B06B 1/06* (2006.01)
(Continued)

(52) U.S. Cl.
CPC ............ *H01L 41/0533* (2013.01); *A61B 8/14* (2013.01); *A61B 8/4427* (2013.01); *A61B 8/4444* (2013.01); *A61B 8/4494* (2013.01); *B06B 1/0629* (2013.01); *B06B 1/0696* (2013.01); *B41J 2/14233* (2013.01); *H01L 41/04* (2013.01); *H01L 41/042* (2013.01); *H01L 41/0477* (2013.01); *H01L 41/0805* (2013.01);
(Continued)

(58) Field of Classification Search
CPC .............. H01L 41/0533; H01L 41/042; H01L 41/0477; H01L 41/0973; H01L 41/047; H01L 41/053
USPC .................................................. 310/348, 365
See application file for complete search history.

(56) References Cited

U.S. PATENT DOCUMENTS 9,375,921 B2 6/2016 Naganuma et al.
9,592,031 B2 3/2017 Kiyose et al.
(Continued)

FOREIGN PATENT DOCUMENTS

JP 2014-195494 A 10/2014
JP 2015-015316 A 1/2015
(Continued)

*Primary Examiner* — Derek J Rosenau
(74) *Attorney, Agent, or Firm* — Harness, Dickey & Pierce, P.L.C.

(57) ABSTRACT

A piezoelectric element includes a piezoelectric element main body as a laminated body of a first electrode layer, a piezoelectric layer disposed on the first electrode layer, and a second electrode layer disposed on the piezoelectric layer, and a metal layer disposed on the second electrode layer via an insulating layer, the piezoelectric layer extends from an inner side of at least a part of an overlapping part of an outer peripheral edge of the second electrode layer overlapping an outer peripheral edge of the piezoelectric element main body to an outer side, and the metal layer and the insulating layer extend from an inner side of at least a part of the overlapping part to an outer side to overlap the piezoelectric layer on an outer side of an outer peripheral edge of the second electrode layer.

13 Claims, 14 Drawing Sheets

(51) Int. Cl.
  *H01L 41/053*  (2006.01)
  *H01L 41/047*  (2006.01)
  *H01L 41/09*  (2006.01)
  *A61B 8/14*  (2006.01)
  *A61B 8/00*  (2006.01)
  *H01L 41/08*  (2006.01)
  *B41J 2/14*  (2006.01)

(52) U.S. Cl.
  CPC ....... *H01L 41/0973* (2013.01); *B41J 2/14201* (2013.01); *B41J 2002/14241* (2013.01); *B41J 2002/14419* (2013.01); *B41J 2202/03* (2013.01)

(56) References Cited

U.S. PATENT DOCUMENTS

| | | | |
|---|---|---|---|
| 2009/0026887 A1* | 1/2009 | Fujii | B41J 2/14233 310/330 |
| 2010/0149284 A1* | 6/2010 | Yazaki | B41J 2/14233 347/71 |
| 2014/0296716 A1 | 10/2014 | Kiyose et al. | |
| 2015/0094590 A1 | 4/2015 | Kiyose et al. | |
| 2016/0067968 A1 | 3/2016 | Naganu Ma et al. | |
| 2017/0128047 A1 | 5/2017 | Kiyose et al. | |
| 2017/0352796 A1* | 12/2017 | Naono | H01L 41/09 |

FOREIGN PATENT DOCUMENTS

| | | |
|---|---|---|
| JP | 2015-066202-qqqA | 4/2015 |
| JP | 2015-204544 A | 11/2015 |
| JP | 2016-058715 A | 4/2016 |

\* cited by examiner

PIEZOELECTRIC ELEMENT, PIEZOELECTRIC ACTUATOR, ULTRASONIC PROBE, ULTRASONIC DEVICE, ELECTRONIC APPARATUS, LIQUID JET HEAD, AND LIQUID JET DEVICE

BACKGROUND

1. Technical Field

The present invention relates to a piezoelectric element, a piezoelectric actuator, an ultrasonic probe, an ultrasonic device, an electronic apparatus, a liquid jet head, and a liquid jet device.

2. Related Art

In the past, there has been known an ultrasonic transducer equipped with a vibrating film, and a piezoelectric element disposed on the vibrating film (e.g., JP-A-2014-195494).

In such an ultrasonic transducer as described in JP-A-2014-195494, the piezoelectric element is constituted by a lower electrode, a piezoelectric film, and an upper electrode stacked on one another. In the stacking direction, the area where the lower electrode, the piezoelectric film, and the upper electrode overlap each other is an area (hereinafter also referred to as an active part) to be deformed in response to application of a voltage between the electrodes. For example, the ultrasonic transducer described above makes the vibrating film vibrate due to the deformation of the active part according to the application of the voltage between the electrodes to transmit an ultrasonic wave.

Here, in the piezoelectric element described in JP-A-2014-195494, stress is concentrated in the boundary position between the active part and a part (inactive part) other than the active part in a plan view viewed from the stacking direction when driving the piezoelectric element. Outside of the boundary position, in a position covered with the upper electrode, the stress between the active part and the inactive part is eased by the elasticity of the upper electrode.

In contrast, in the case in which the piezoelectric film is disposed so as to straddle a position overlapping the end edge of the upper electrode outside of the boundary position, since the position corresponding to the inactive part of the piezoelectric film is not covered with the upper electrode, there is a possibility that cracks are caused in the piezoelectric film in the boundary position due to the concentration of the stress described above. Further, in the case in which water infiltrates in the cracks caused in the piezoelectric film, there is a possibility that the piezoelectric film burns out due to the energization between the lower electrode and the upper electrode, and thus, the performance of the piezoelectric element deteriorates.

SUMMARY

An advantage of some aspects of the invention is to provide a piezoelectric element, a piezoelectric actuator, an ultrasonic probe, an ultrasonic device, an electronic apparatus, a liquid jet head, and the liquid jet device as application examples and embodiments capable of preventing the cracks in the piezoelectric film from occurring.

A piezoelectric element according to an application example of the invention includes a piezoelectric element main body having a first electrode layer, a piezoelectric layer, and a second electrode layer stacked in sequence, and a metal layer disposed on the second electrode layer via an insulating layer, the piezoelectric layer has an extending part extending from the piezoelectric element main body to an outer side of an outer peripheral edge of the second electrode layer in a plan view viewed from a stacking direction of the first electrode layer, the piezoelectric layer, and the second electrode layer, and the metal layer and the insulating layer are disposed from the second electrode layer to the extending part of the piezoelectric element main body in the plan view.

In this application example, the piezoelectric element is provided with the piezoelectric element main body having the first electrode layer, the piezoelectric layer, and the second electrode layer stacked in sequence, and the metal layer disposed on the second electrode layer via the insulating layer. Among these constituents, the piezoelectric layer has the extending part extending from the piezoelectric element main body to the outer side of the outer peripheral edge of the second electrode layer in the plan view in the stacking direction. In other words, the outer peripheral edge of the second electrode has the overlapping part overlapping the piezoelectric element main body. Further, the piezoelectric layer is disposed so as to straddle the overlapping part.

Here, the extending part is not provided with the second electrode layer. Therefore, when the piezoelectric element main body is driven, the stress is apt to be concentrated on the position overlapping the overlapping part of the piezoelectric layer as described above in the plan view. In contrast, in this application example, the metal layer and the insulating layer are disposed from the second electrode layer to the extending part of the piezoelectric element main body in the plan view. In other words, the metal layer is disposed so as to straddle the overlapping part in the plan view. In such a configuration, due to the elasticity of the metal layer, the stress in the piezoelectric layer can be relaxed, and thus, the cracks described above can be prevented from occurring.

Further, by disposing the metal layer at the position overlapping the overlapping part, it is possible to improve the water-resistance. Thus, it is possible to prevent the burnout of the piezoelectric layer due to the short circuit between the outer peripheral edge of the second electrode layer and the first electrode layer from occurring in the overlapping part, and thus, the performance degradation of the piezoelectric element main body can be prevented.

In the piezoelectric element according to the application example, it is preferable that the metal layer is formed using at least one of Pt, Ir, Ti, Zr, Au, Ni, NiCr, and TiW.

In the application example with this configuration, it is possible to provide the metal layer with the elasticity capable of preventing the cracks of the piezoelectric layer from occurring while allowing the deformation of the piezoelectric layer. Thus, the cracks can more appropriately be prevented from occurring in the piezoelectric layer.

In the piezoelectric element according to the application example, it is preferable that the insulating layer is formed using at least one of $Al_2O_3$, $TaO_x$, $HfO_x$, and $SiO_2$.

In the application example with this configuration, it is possible to improve the adhesiveness to the piezoelectric layer, the second electrode layer, and the metal layer, and it is possible to more surely relax the stress of the piezoelectric layer using the metal layer. Further, in the application example with this configuration, it is possible to improve the water-resistance of the insulating layer compared to the case of forming the insulating layer using, for example, resin. Therefore, it is possible to preferably prevent the burnout of the piezoelectric layer described above.

A piezoelectric actuator according to an application example of the invention includes a piezoelectric element main body having a first electrode layer, a piezoelectric layer, and a second electrode layer stacked in sequence, a metal layer disposed on the second electrode layer via an insulating layer, and a drive part driven by the piezoelectric element main body, the piezoelectric layer has an extending part extending from the piezoelectric element main body to an outer side of an outer peripheral edge of the second electrode layer in a plan view viewed from a stacking direction of the first electrode layer, the piezoelectric layer, and the second electrode layer, and the metal layer and the insulating layer are disposed from the second electrode layer to the extending part of the piezoelectric element main body in the plan view.

In this application example, the piezoelectric actuator is provided with the piezoelectric element main body having the first electrode layer, the piezoelectric layer, and the second electrode layer stacked in sequence, and the metal layer disposed on the second electrode layer via the insulating layer. Among these constituents, the piezoelectric layer has the extending part extending from the piezoelectric element main body to the outer side of the outer peripheral edge of the second electrode layer in the plan view in the stacking direction. Further, the metal layer and the insulating layer are disposed from the second electrode layer to the extending part of the piezoelectric element main body in the plan view.

In the piezoelectric actuator according to this application example configured in such a manner, similarly to the application examples described above, due to the metal layer disposed so as to overlap the piezoelectric layer straddling the overlapping part in the plan view, the stress in the piezoelectric layer can be relaxed, and thus, the cracks described above can be prevented from occurring.

Further, by disposing the metal layer at the position overlapping the overlapping part, it is possible to improve the water-resistance. Thus, it is possible to prevent the burnout of the piezoelectric layer due to the short circuit between the outer peripheral edge of the second electrode layer and the first electrode layer from occurring in the overlapping part, and thus, the performance degradation of the piezoelectric element main body can be prevented.

In the piezoelectric actuator according to the application example, it is preferable that the drive section is a vibrating film, and the piezoelectric element main body is disposed on the vibrating film.

In the application example with this configuration, the piezoelectric element main body is disposed on the vibrating film to vibrate the vibrating film. In such a configuration, the vibrating film is vibrated in the stacking direction in accordance with the drive of the piezoelectric element main body. Therefore, at least a part of the piezoelectric layer also deforms in the stacking direction, and thus, the stress acts on the piezoelectric layer. In the application example with this configuration, as described above, the metal layer is disposed so as to overlap the piezoelectric layer straddling the overlapping part. Therefore, even in the case in which the piezoelectric layer deforms in the stacking direction, the concentration of the stress on the overlapping part of the piezoelectric layer can be prevented.

In the piezoelectric actuator according to the application example, it is preferable that there is further included a substrate having an aperture to be blocked by the vibrating film, and adapted to support the vibrating film, at least a part of the piezoelectric element main body overlaps the aperture in the plan view, and the extending part is located on an outer side of the aperture in the plan view.

In the application example with this configuration, the substrate has an aperture for supporting the vibrating film and is blocked by the vibrating film. In other words, the position overlapping the aperture in the vibrating film becomes the deformable and flexible part. Further, at least a part of the piezoelectric element main body is disposed on the flexible part. Further, the extending part is disposed outside the aperture, namely the area (a stationary part) other than the flexible part of the vibrating film. Therefore, the overlapping part is located outside the aperture. In such a configuration, in the overlapping part, the piezoelectric layer is disposed on the stationary part of the vibrating film, and does not deform in the stacking direction. Therefore, the concentration of the stress in the piezoelectric layer in the overlapping part can further be prevented.

In the piezoelectric actuator according to the application example, it is preferable that the metal layer is located outside of the aperture in the plan view.

In the application example with this configuration, the metal layer is located outside the aperture in the plan view. Here, in the case in which the metal layer is disposed on the flexible part of the vibrating film, there is a possibility that the deformation of the piezoelectric element main body and the vibrating film in the stacking direction is hindered by the metal layer. For example, there is a possibility that the amplitude in the stacking direction when driving the piezoelectric element main body is decreased. In contrast, in the application example with this configuration, since the metal layer is located outside the aperture, it is possible to prevent the deformation of the piezoelectric element main body and the vibrating film in the stacking direction from being hindered by the metal layer.

An ultrasonic probe according to an application example of the invention includes a piezoelectric element main body having a first electrode layer, a piezoelectric layer, and a second electrode layer stacked in sequence, a metal layer disposed on the second electrode layer via an insulating layer, and a vibrating film on which the piezoelectric element main body is disposed, the piezoelectric layer has an extending part extending from the piezoelectric element main body to an outer side of an outer peripheral edge of the second electrode layer in a plan view viewed from a stacking direction of the first electrode layer, the piezoelectric layer, and the second electrode layer, and the metal layer and the insulating layer are disposed from the second electrode layer to the extending part of the piezoelectric element main body in the plan view.

In this application example, the ultrasonic probe is provided with the piezoelectric element main body having the first electrode layer, the piezoelectric layer, and the second electrode layer stacked in sequence, and the metal layer disposed on the second electrode layer via the insulating layer. Among these constituents, the piezoelectric layer has the extending part extending from the piezoelectric element main body to the outer side of the outer peripheral edge of the second electrode layer in the plan view in the stacking direction. Further, the metal layer and the insulating layer are disposed from the second electrode layer to the extending part of the piezoelectric element main body in the plan view.

In the ultrasonic probe according to this application example configured in such a manner, similarly to the application examples described above, due to the metal layer disposed so as to overlap the piezoelectric layer straddling the overlapping part in the plan view, the stress in the piezoelectric layer can be relaxed, and thus, the cracks described above can be prevented from occurring.

Further, by disposing the metal layer at the position overlapping the overlapping part, it is possible to improve the water-resistance. Thus, it is possible to prevent the burnout of the piezoelectric layer due to the short circuit between the outer peripheral edge of the second electrode layer and the first electrode layer from occurring in the overlapping part, and thus, the performance degradation of the piezoelectric element main body can be prevented.

An ultrasonic device according to an application example of the invention includes a piezoelectric element main body having a first electrode layer, a piezoelectric layer, and a second electrode layer stacked in sequence, a metal layer disposed on the second electrode layer via an insulating layer, a vibrating film on which the piezoelectric element main body is disposed, and a control section adapted to control the piezoelectric element main body, the piezoelectric layer has an extending part extending from the piezoelectric element main body to an outer side of an outer peripheral edge of the second electrode layer in a plan view viewed from a stacking direction of the first electrode layer, the piezoelectric layer, and the second electrode layer, and the metal layer and the insulating layer are disposed from the second electrode layer to the extending part of the piezoelectric element main body in the plan view.

In the application example, the ultrasonic device is provided with the piezoelectric element main body having the first electrode layer, the piezoelectric layer, and the second electrode layer stacked in sequence, and the metal layer disposed on the second electrode layer via the insulating layer. Among these constituents, the piezoelectric layer has the extending part extending from the piezoelectric element main body to the outer side of the outer peripheral edge of the second electrode layer in the plan view in the stacking direction. Further, the metal layer and the insulating layer are disposed from the second electrode layer to the extending part of the piezoelectric element main body in the plan view.

In the ultrasonic device according to this application example configured in such a manner, similarly to the application examples described above, due to the metal layer disposed so as to overlap the piezoelectric layer straddling the overlapping part in the plan view, the stress in the piezoelectric layer can be relaxed, and thus, the cracks described above can be prevented from occurring.

Further, by disposing the metal layer at the position overlapping the overlapping part, it is possible to improve the water-resistance. Thus, it is possible to prevent the burnout of the piezoelectric layer due to the short circuit between the outer peripheral edge of the second electrode layer and the first electrode layer from occurring in the overlapping part, and thus, the performance degradation of the piezoelectric element main body can be prevented.

An electronic apparatus according to an application example of the invention includes a piezoelectric element main body having a first electrode layer, a piezoelectric layer, and a second electrode layer stacked in sequence, a metal layer disposed on the second electrode layer via an insulating layer, a drive part driven by the piezoelectric element main body; and a control section adapted to control the piezoelectric element main body, the piezoelectric layer has an extending part extending from the piezoelectric element main body to an outer side of an outer peripheral edge of the second electrode layer in a plan view viewed from a stacking direction of the first electrode layer, the piezoelectric layer, and the second electrode layer, and the metal layer and the insulating layer are disposed from the second electrode layer to the extending part of the piezoelectric element main body in the plan view.

In this application example, the electronic apparatus is provided with the piezoelectric element main body having the first electrode layer, the piezoelectric layer, and the second electrode layer stacked in sequence, and the metal layer disposed on the second electrode layer via the insulating layer. Among these constituents, the piezoelectric layer has the extending part extending from the piezoelectric element main body to the outer side of the outer peripheral edge of the second electrode layer in the plan view in the stacking direction. Further, the metal layer and the insulating layer are disposed from the second electrode layer to the extending part of the piezoelectric element main body in the plan view.

In the electronic apparatus according to this application example configured in such a manner, similarly to the application examples described above, due to the metal layer disposed so as to overlap the piezoelectric layer straddling the overlapping part in the plan view, the stress in the piezoelectric layer can be relaxed, and thus, the cracks described above can be prevented from occurring.

Further, by disposing the metal layer at the position overlapping the overlapping part, it is possible to improve the water-resistance. Thus, it is possible to prevent the burnout of the piezoelectric layer due to the short circuit between the outer peripheral edge of the second electrode layer and the first electrode layer from occurring in the overlapping part, and thus, the performance degradation of the piezoelectric element main body can be prevented.

A liquid jet head according to an application example of the invention includes the piezoelectric actuator according to the application examples described above.

In this application example, the liquid jet head is capable of relaxing the stress in the piezoelectric layer, and thus, preventing the cracks described above from occurring due to the metal layer disposed so as to overlap the piezoelectric layer straddling the overlapping part in the plan view similarly to the application examples described above. Further, by disposing the metal layer at the position overlapping the overlapping part, it is possible to improve the water-resistance. Thus, it is possible to prevent the burnout of the piezoelectric layer due to the short circuit between the outer peripheral edge of the second electrode layer and the first electrode layer from occurring in the overlapping part, and thus, the performance degradation of the piezoelectric element main body can be prevented.

A liquid jet device according to an application example of the invention includes the liquid jet head according to the application examples described above.

In this application example, the liquid jet device is capable of relaxing the stress in the piezoelectric layer, and thus, preventing the cracks described above from occurring due to the metal layer disposed so as to overlap the piezoelectric layer straddling the overlapping part in the plan view similarly to the application examples described above. Further, by disposing the metal layer at the position overlapping the overlapping part, it is possible to improve the water-resistance. Thus, it is possible to prevent the burnout of the piezoelectric layer due to the short circuit between the outer peripheral edge of the second electrode layer and the first electrode layer from occurring in the overlapping part, and thus, the performance degradation of the piezoelectric element main body can be prevented.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

First Embodiment

An ultrasonic measurement device according to a first embodiment of the invention will hereinafter be described with reference to the accompanying drawings.

Figure 1:
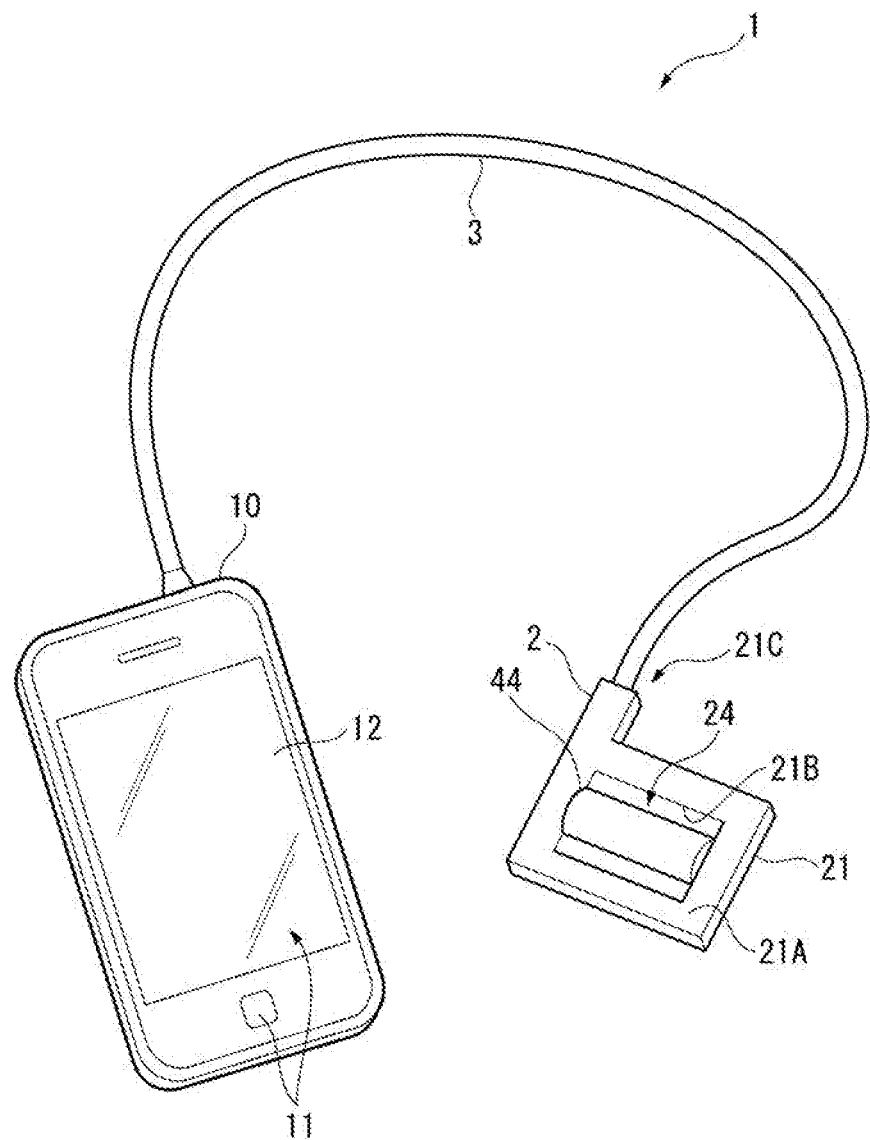
FIG. 1 is a perspective view showing a schematic configuration of an ultrasonic measurement device according to a first embodiment of the invention.

FIG. 1 is a perspective view showing a schematic configuration of an ultrasonic measurement device 1.

As shown in FIG. 1, the ultrasonic measurement device 1 is provided with an ultrasonic probe 2, and a control device 10 electrically connected to the ultrasonic probe 2 via a cable 3.

The ultrasonic measurement device 1 transmits an ultrasonic wave from the ultrasonic probe 2 to the inside of a living body (e.g., a human body) with the ultrasonic probe 2 having contact with a surface of the living body. Further, the ultrasonic measurement device 1 receives the ultrasonic wave reflected by a part in the living body using the ultrasonic probe 2, and then, for example, obtains an internal tomographic image of the inside of the living body to measure the state (e.g., blood flow) of the part in the living body based on the received signal.

Configuration of Control Device

As shown in FIG. 1, the control device 10 corresponds to a control section, and is provided with an operating section 11 including buttons or touch panel, and a display section 12. Further, although not shown in the drawings, the control device 10 is provided with a storage section formed of a memory or the like, and an arithmetic section constituted by a central processing unit (CPU) or the like. The control device 10 makes the arithmetic section execute a variety of programs stored in the storage section to thereby control the ultrasonic measurement device 1. For example, the control device 10 outputs a command for controlling the drive of the ultrasonic probe 2, forms an image of the internal structure of the living body and then makes the display section 12 display the image, and measures the living body information such as the blood flow to make the display section 12 display the living body information. As such a control device 10, a terminal device such as a tablet terminal, a smartphone, or a personal computer can be used, and a dedicated terminal device for operating the ultrasonic probe 2 can also be used.

Configuration of Ultrasonic Probe

Figure 2:
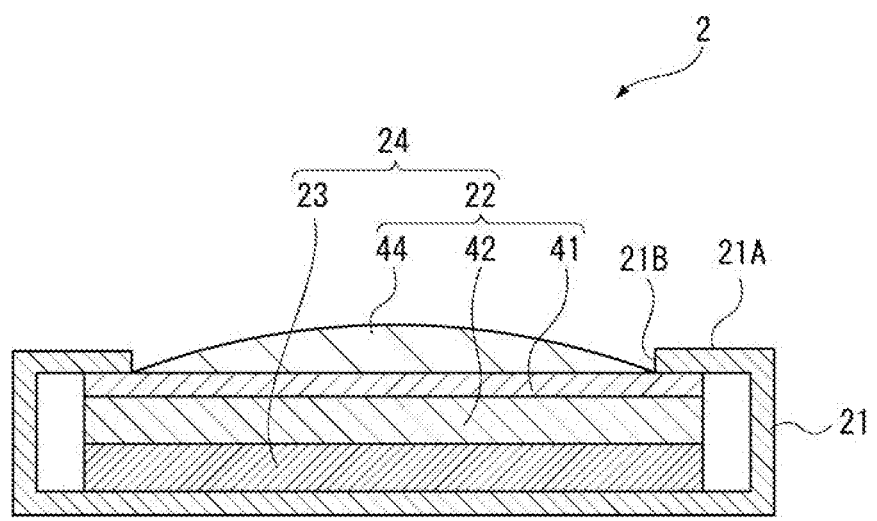
FIG. 2 is a cross-sectional view showing a schematic configuration of an ultrasonic probe according to the first embodiment.

FIG. 2 is a cross-sectional view showing a schematic configuration of an ultrasonic probe 2.

As shown in FIG. 2, the ultrasonic probe 2 is provided with a housing 21, an ultrasonic device 22 housed inside the housing 21, and a circuit board 23 provided with a driver circuit for controlling the ultrasonic device 22. It should be noted that the ultrasonic sensor 24 is constituted by the ultrasonic device 22 and the circuit board 23, and the ultrasonic sensor 24 constitutes an ultrasonic module.

Configuration of Housing

As shown in FIG. 1, the housing 21 is formed to have a box-like shape having, for example, a rectangular planar shape, and on one surface (a sensor surface 21A) perpendicular to the thickness direction, there is disposed a sensor window 21B, and a part of the ultrasonic device 22 is exposed therefrom. Further, in a part (a side surface in the example shown in FIG. 1) of the housing 21, there is provided a through hole 21C for the cable 3, and the cable 3 is connected to the circuit board 23 located inside the housing 21 through the through hole 21C. Further, the gap between the cable 3 and the through hole 21C is filled with, for example, a resin material to thereby ensure waterproofness.

It should be noted that although in the present embodiment there is shown a configuration example in which the ultrasonic probe 2 and the control device 10 are connected to each other using the cable 3, the configuration is not limited to this example, and it is also possible to, for example, connect the ultrasonic probe 2 and the control device 10 to each other with wireless communication, or dispose a variety of constituents of the control device 10 inside the ultrasonic probe 2.

Configuration of Circuit Board

The circuit board 23 is electrically connected to signal terminals 413 and common terminals 415 (see FIG. 3) of the ultrasonic device 22 to control the ultrasonic device 22 based on the control by the control device 10.

Specifically, the circuit board 23 is provided with a transmission circuit, a reception circuit, and the like. The transmission circuit outputs a drive signal for making the ultrasonic device 22 perform ultrasonic transmission. The reception circuit obtains the reception signal output from the ultrasonic device 22, which has received the ultrasonic wave, then performs an amplification process, an A-D conversion process, a phasing addition process and so on of the reception signal, and then outputs the result to the control device 10.

Configuration of Ultrasonic Device

Figure 3:
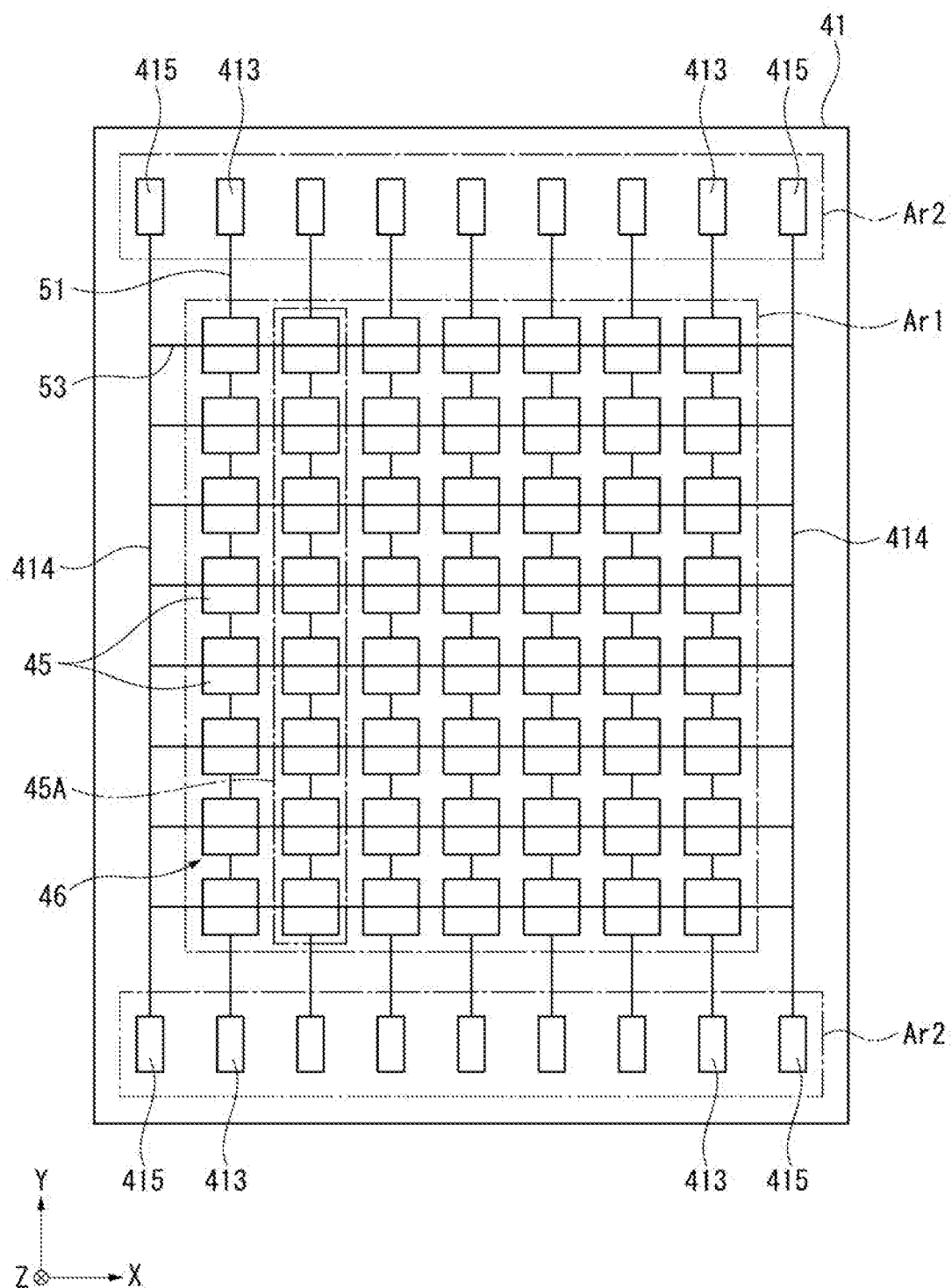
FIG. 3 is a plan view schematically showing an element substrate in an ultrasonic device according to the first embodiment.

FIG. 3 is a diagram schematically showing an element substrate 41 constituting the ultrasonic device 22 as viewed from a sealing plate 42 side.

Figure 4:
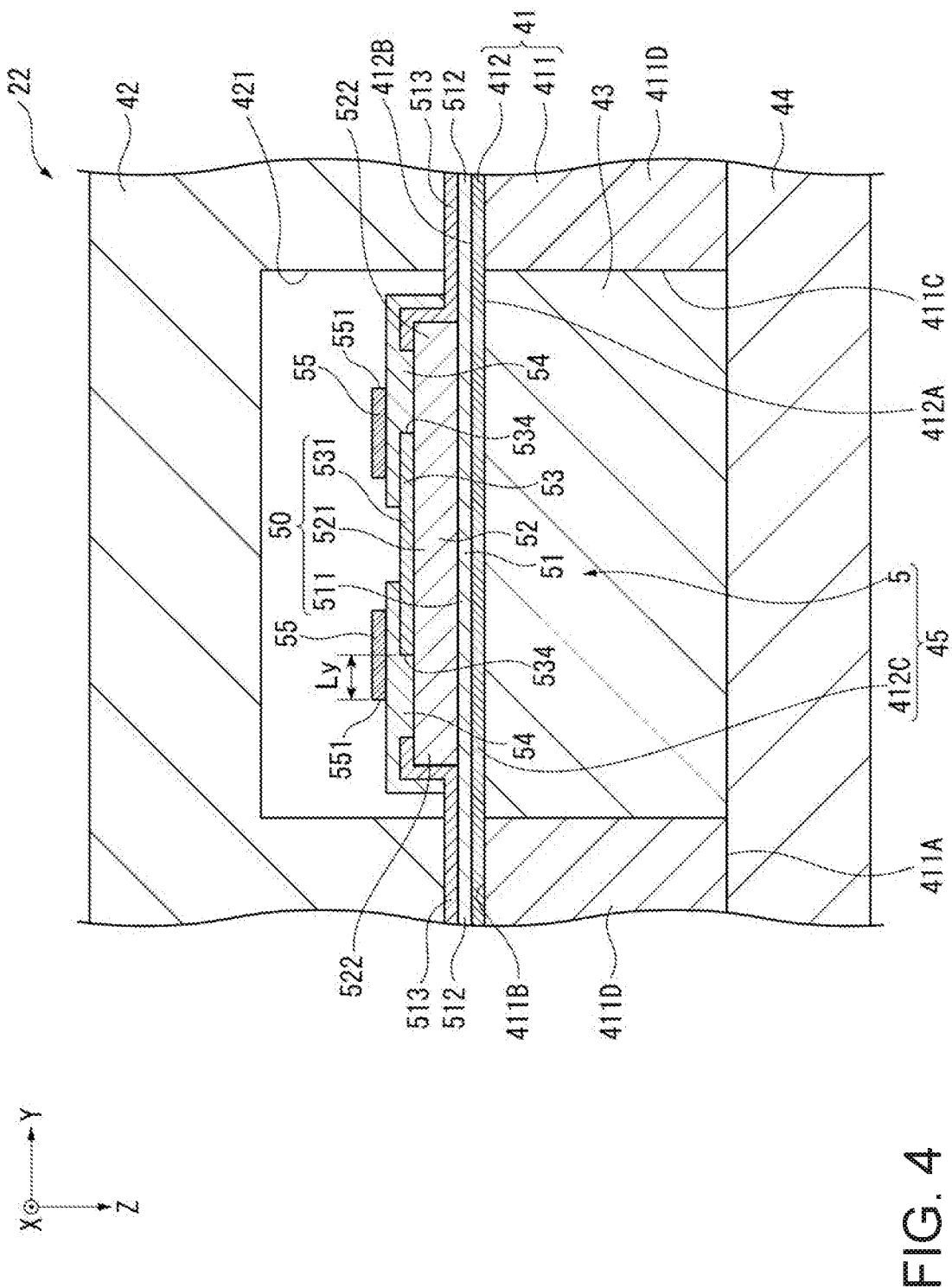
FIG. 4 is a cross-sectional view schematically showing an ultrasonic transducer according to the first embodiment.
Figure 5:
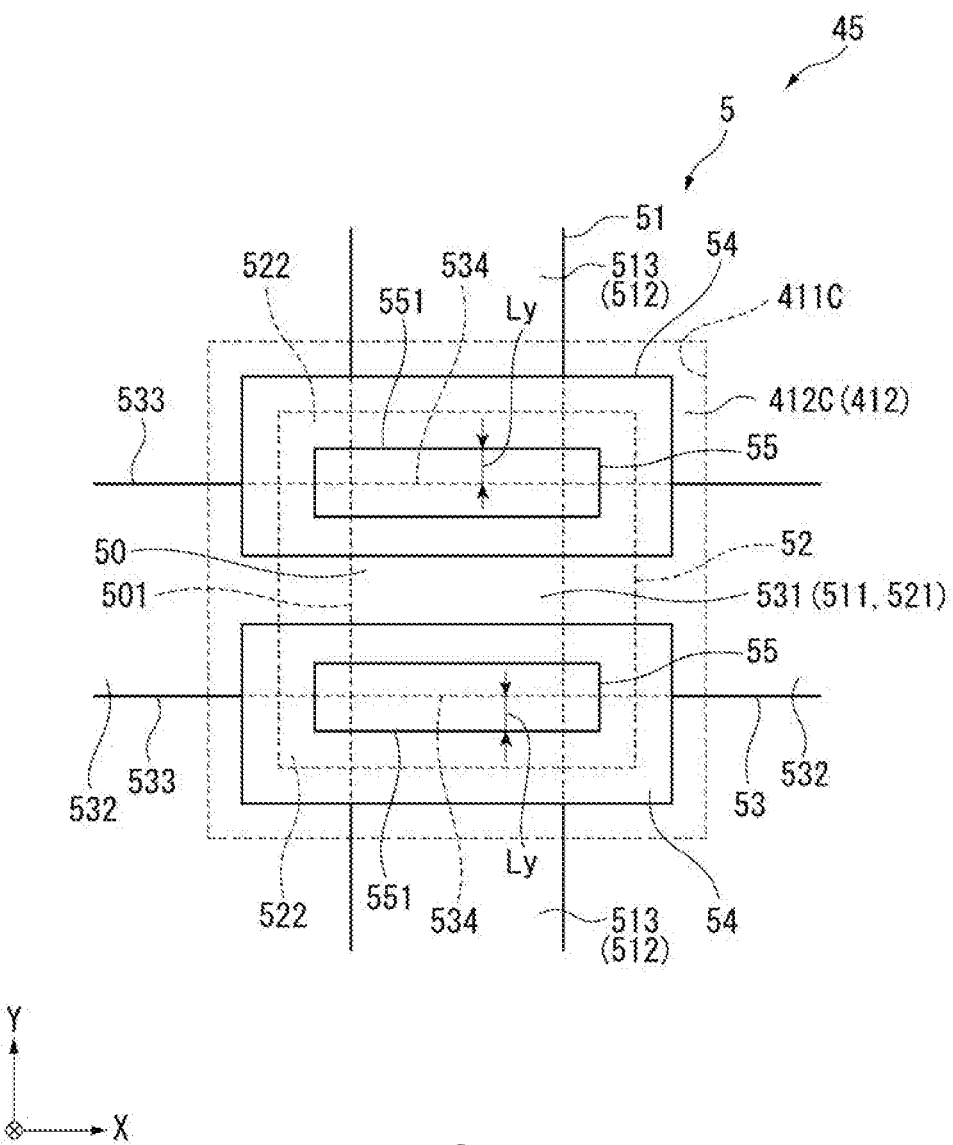
FIG. 5 is a plan view schematically showing the ultrasonic transducer according to the first embodiment.

Further, FIG. 4 is a cross-sectional view of an ultrasonic transducer 45, and FIG. 5 is a plan view schematically showing the ultrasonic transducer 45 provided to the element substrate 41.

As shown in FIG. 2, the ultrasonic device 22 is configured including the element substrate 41, the sealing plate 42, an acoustic layer 43 (see FIG. 4), and an acoustic lens 44.

Configuration of Element Substrate

As shown in FIG. 3, in the plan view (hereinafter also referred to simply as a plan view) of the element substrate viewed from the substrate thickness direction (a Z direction), in an array area Ar1 at the center of the element substrate 41, there is disposed an ultrasonic transducer array 46 including the ultrasonic transducers 45 for performing transmission and reception of the ultrasonic wave. The ultrasonic transducer array 46 is configured as a one-dimensional array having the plurality of ultrasonic transducers 45 arranged in a matrix. Specifically, the ultrasonic transducer array 46 has a plurality of transmission/reception rows 45A each functioning as a 1-CH transmission/reception channel. These transmission/reception rows 45A are each constituted by a plurality of ultrasonic transducers 45 arranged along the Y direction (a slicing direction), and are arranged in the X direction (a scanning direction). It should be noted that in FIG. 3, the number of the ultrasonic transducers 45 arranged is reduced for the sake of convenience of explanation, but in reality, there are a larger number of ultrasonic transducers 45.

As shown in FIG. 4, the element substrate 41 is provided with a substrate main body 411, a vibrating film 412 disposed on the sealing plate 42 side (−Z side) of the substrate main body 411, and a piezoelectric element 5 disposed on the vibrating film 412.

Here, in the following description, a surface on the acoustic lens 44 side of the substrate main body 411 is referred to as a front surface 411A, and a surface on the sealing plate 42 side is referred to as a back surface 411B. Further, a surface on the opposite side of the vibrating film 412 to the sealing plate 42 is referred to as an ultrasonic wave transmission/reception surface 412A, and a surface on the sealing plate 42 side is referred to as an operating surface 412B.

The substrate main body 411 is a substrate for supporting the vibrating film 412, and is formed of a semiconductor substrate made of, for example, Si. To the substrate main body 411, there are provided apertures 411C corresponding respectively to the ultrasonic transducers 45.

The vibrating film 412 is formed of, for example, $SiO_2$ or a laminated body of $SiO_2$ and $ZrO_2$, and is disposed on the back surface 411B of the substrate main body 411. The thickness dimension of the vibrating film 412 is small with respect to that of the substrate main body 411. The vibrating film 412 is supported by a wall 411D constituting the aperture 411C, and has a flexible part 412C (e.g., a part that flexes) which blocks the back surface 411B side of the aperture 411C. In other words, the aperture 411C defines the outer edge of the flexible part 412C as a vibrating area of the vibrating film 412.

Further, on the operating surface 412B of the vibrating film 412 blocking each of the apertures 411C, there is disposed a piezoelectric element main body 50 constituting the piezoelectric element 5. It should be noted that although described later in detail, the piezoelectric element 5 is provided with the piezoelectric element main body 50, an insulating layer 54, and a metal layer 55. Further, the piezoelectric element main body 50 is configured as a laminated body having a lower electrode 51, a piezoelectric film 52, and an upper electrode 53 stacked in sequence (e.g., the piezoelectric film 52 is stacked directly on the lower electrode 51, and the upper electrode 53 is stacked directly on the piezoelectric film 52). Each of the ultrasonic transducers 45 is constituted by the flexible part 412C of the vibrating film 412 and the piezoelectric element 5.

In such an ultrasonic transducer 45, by applying a pulse-wave voltage having a predetermined frequency between the lower electrode 51 and the upper electrode 53, the flexible part 412C of the vibrating film 412 spanning an opening region of the aperture 411C is vibrated to transmit the ultrasonic wave from the ultrasonic wave transmission/reception surface 412A side. Further, when the flexible part 412C of the vibrating film 412 is vibrated by the ultrasonic wave, which is reflected by an object, and then enters the ultrasonic wave transmission/reception surface 412A, an electrical potential difference occurs between an upper part and a lower part of the piezoelectric film 52. Therefore, by detecting the electrical potential difference occurring between the lower electrode 51 and the upper electrode 53, the ultrasonic wave is received and detected.

Here, as shown in FIG. 3, the lower electrode 51 is formed to extend linearly along the Y direction with respect to each of the 1-CH transmission/reception rows 45A. Both ends (ends on the ±Y sides) of the lower electrode 51 are connected to the respective signal terminals 413 in a terminal area Ar2. The signal terminals 413 are electrically connected to the circuit board 23.

Further, the upper electrode 53 is formed to extend linearly along the X direction, and connects the transmission/reception rows 45A arranged in the X direction. Further, the ends on the ±X sides of the upper electrode 53 are respectively connected to common electrode lines 414. The common electrode lines 414 each connect the upper electrodes 53, which are arranged along the Y direction, to each other. Further, both ends (ends on the ±Y sides) of the common electrode line 414 are connected to the respective common terminals 415 in the terminal area Ar2. The common terminals 415 are connected to, for example, a reference electrical potential circuit (not shown) of the circuit board 23, and are set to the reference electrical potential.

Configuration of Sealing Plate

The sealing plate 42 is formed to have the same shape when viewed from the thickness direction as that of, for example, the element substrate 41, and is formed of a semiconductor substrate made of Si or the like, or an insulator substrate. It should be noted that the material and the thickness of the sealing plate 42 affect the frequency characteristics of the ultrasonic transducer 45, and are therefore preferably set based on the central frequency of the ultrasonic wave transmitted/received by the ultrasonic transducer 45.

The sealing plate 42 has a plurality of concave grooves 421 (see FIG. 4), which correspond to the apertures 411C, in an area opposed to the array area Ar1 of the element substrate 41. Thus, a gap having a predetermined dimension is provided between the element substrate 41 and the area (inside the aperture 411C) where the flexible part 412C is formed of the vibrating film 412, and thus, the vibration of the vibrating film 412 is prevented from being hindered. Further, the problem (cross talk) that the back wave from one ultrasonic transducer 45 enters another ultrasonic transducer 45 adjacent to that ultrasonic transducer 45 can be prevented from occurring.

Further, when the vibrating film 412 vibrates, an ultrasonic wave is also emitted toward the sealing plate 42 side (the back surface 411B side) as the back wave in addition to the aperture 411C side (the ultrasonic wave transmission/reception surface 412A side). The back wave is reflected by the sealing plate 42, and is then emitted again toward the vibrating film 412 side via the gap. On this occasion, if the phase of the reflected back wave and the phase of the ultrasonic wave emitted from the vibrating film 412 toward the ultrasonic wave transmission/reflection surface 412A side are shifted from each other, the ultrasonic wave attenuates. Therefore, in the present embodiment, the groove depth of each of the concave grooves 421 is set so that the acoustic distance in the gap between the element substrate 41 and the sealing plate 42 becomes an odd multiple of $\lambda/4$ defining the wavelength of the ultrasonic wave as $\lambda$. In other words, the thickness dimensions of the variety of parts of the element substrate 41 and the sealing plate 42 are set taking the wavelength $\lambda$ of the ultrasonic wave emitted from the ultrasonic transducers 45 into consideration.

Further, a connecting section for connecting the terminals 413 and 415 to the circuit board 23 is provided to the sealing plate 42 at a position opposed to the terminal area Ar2 of the element substrate 41. As the connecting section, there is cited a configuration including, for example, an aperture provided to the element substrate 41, and a wiring member such as flexible printed circuits (FPC), cable lines, or wires for connecting the terminals 413, 415 and the circuit board 23 to each other via the aperture.

Configuration of Acoustic Layer and Acoustic Lens

The acoustic layer 43 is disposed on the ultrasonic wave transmission/reception surface 412A side. In other words, the aperture 411C is filled with the acoustic layer 43.

The acoustic lens 44 is disposed on the front surface 411A side of the element substrate 41, namely the +Z side of the element substrate 41 and the acoustic layer 43. The acoustic lens 44 contacts the living body surface, and converges the ultrasonic wave, which has been transmitted from the ultrasonic transducer 45, inside the living body. Further, the acoustic lens 44 makes the ultrasonic wave, which has been reflected inside the living body, propagate to the ultrasonic transducer 45 via the acoustic layer 43.

The acoustic impedance of the acoustic layer 43 and the acoustic lens 44 is set to a value close to the acoustic impedance of the living body. Thus, it is possible for the acoustic layer 43 and the acoustic lens 44 to efficiently propagate the ultrasonic wave emitted from the ultrasonic transducer 45 to the living body, and further to propagate the ultrasonic wave, which has been reflected inside the living body, to the ultrasonic transducer 45 with efficiency.

Configuration of Piezoelectric Element

As shown in FIG. 4 and FIG. 5, the piezoelectric element 5 is provided with the piezoelectric element main body 50 having the lower electrode 51, the piezoelectric film 52, and the upper electrode 53 stacked in sequence, the insulating layer 54, and the metal layer 55.

The piezoelectric element main body 50 is provided to the flexible part 412C corresponding to the drive section, and is configured including a lower electrode main body 511, a piezoelectric film main body 521, and an upper electrode main body 531 overlap each other in the Z direction (the stacking direction) as described later. In other words, the piezoelectric element main body 50 is an active part deforming in accordance with the voltage applied between the lower electrode 51 and the upper electrode 53.

The lower electrode 51 corresponds to a first electrode layer, and is provided with the lower electrode main body 511, a lower electrode connector 512, and a lower electrode covering 513.

The lower electrode main body 511 overlaps the piezoelectric film 52 and the upper electrode 53 in the plan view, and is disposed on the flexible part 412C of the vibrating film 412. In other words, the lower electrode main body 511 is provided to each of the piezoelectric elements 5.

The lower electrode connector 512 extends along the Y direction from each of the ±Y sides of the lower electrode main body 511 to connect the lower electrode main body parts 511 adjacent to each other out of the plurality of lower electrode main body parts 511 included in the transmission/reception row 45A.

The lower electrode covering 513 is disposed on at least the lower electrode connector 512 along the Y direction. Further, an end in the Y direction of the lower covering 513 is disposed on the piezoelectric film 52. The lower electrode covering 513 functions as a protective film of the lower electrode connector 512. For example, in the case of performing patterning of the upper electrode 53 by etching or the like, deterioration of the lower electrode connector 512 due to over-etching can be suppressed. It should be noted that in this case, the lower electrode covering 513 is formed at the same time as the upper electrode 53.

The upper electrode 53 corresponds to a second electrode layer, and is an electrode common to the ultrasonic transducers 45. As the material of the upper electrode 53, a metal material such as Pt, Ir, Ti, Zr, Au, Ni, NiCr, TiW, Al, or Cu can be used.

The upper electrode 53 is at least partially disposed on the piezoelectric film 52, and has an upper electrode main body 531 and an upper electrode connector 532.

The upper electrode main body 531 overlaps the lower electrode 51 and the piezoelectric film 52 in the plan view. In other words, the lower electrode main body 531 is provided to each of the piezoelectric elements 5.

Here, part (hereinafter also referred to as an overlapping part 534) of the outer peripheral edge 533 of the upper electrode 53 and corresponding to the upper electrode main body 531, extends between the outer peripheral edge(s) 501 of the piezoelectric element main body 50 in the plan view. In other words, the overlapping part (edge) 534 terminates where the upper electrode 53 crosses over each outer peripheral edge 501.

The upper electrode connector 532 extends along the X direction from each of the ±X sides of the upper electrode main body 531 to connect the upper electrode main body parts 531 adjacent to each other in the X direction. Further, the upper electrode connector 532 connects the lower electrode main body parts 511 of the piezoelectric elements 5 on the ±X sides of the plurality of piezoelectric elements 5 disposed on the X direction and the common electrode lines 414 to each other.

The piezoelectric film 52 is formed using, for example, a transition metal oxide having a perovskite structure, more specifically, lead zirconate titanate including Pb, Ti, and Zr.

The piezoelectric film 52 corresponds to the piezoelectric layer, includes a piezoelectric film main body 521 and an extending part 522, and is disposed at a position overlapping the aperture 411C so as to cover a part of the lower electrode 51.

The piezoelectric film main body 521 is a part of the piezoelectric film 52 overlapping the lower electrode main body 511 and the upper electrode main body 531 in the plan view. In other words, the piezoelectric element main body 50 is configured as a laminated body of the lower electrode main body 511, the piezoelectric film main body 521, and the upper electrode main body 531.

The extending part 522 extends from the piezoelectric element main body 50 beyond the outer peripheral edge 533 of the upper electrode 53 in the plan view. In other words, the piezoelectric film 52 is disposed from the inside to the outside of the piezoelectric element main body 50 straddling the overlapping part 534 in the plan view.

The insulating layer 54 is disposed between the upper electrode 53 and the metal layer 55 to isolate the upper electrode 53 and the metal layer 55 from each other. The insulating layer 54 is disposed so as to cover the overlapping part 534 of the upper electrode 53 and the extending part 522. In other words, the insulating layer 54 is disposed from the inside to the outside of the piezoelectric element main body 50 straddling an edge of the overlapping part 534.

The insulating layer 54 is formed using at least one material having an insulating property and a water-resistance such as $Al_2O_3$, $TaO_x$, $HfO_x$, and $SiO_2$. Thus, it is possible to improve the water-resistance in the extending part 522 of the piezoelectric film 52. It should be noted that as the insulating layer 54, it is also possible to use an organic protective film such as a permanent resist or an adhesive besides the above.

The metal layer 55 is disposed on the upper electrode 53 via the insulating layer 54, and is isolated from the upper electrode 53. Further, the metal layer 55 covers at least the overlapping part 534 in the plan view. In other words, the metal layer 55 is disposed from the inside to the outside of the piezoelectric element main body 50 straddling an edge of the overlapping part 534 along the Y direction.

The metal layer 55 is formed so that the thickness dimension is, for example, 100 nm using a variety of types of metal materials such as Pt, Ir, Ti, Zr, Au, Ni, NiCr, or TiW.

As shown in FIG. 5, the width dimension in the X direction of the metal layer 55 is larger than at least the width dimension of the overlapping part 534 (i.e., the lower electrode main body 511).

Further, as shown in FIG. 4, the end edge (hereinafter also referred to as a Y-side end edge 551) in the Y direction of the metal layer 55 is located between the overlapping part 534 and the lower electrode covering 513 in the Y direction. In other words, the metal layer 55 extends along the Y direction to a position prior to overlapping the lower electrode covering 513.

Here, the projecting amount Ly of the metal layer 55 with respect to the overlapping part 534 is, for example, no smaller than 100 nm ad no larger than 3 μm in the Y direction.

By setting the projecting amount to be no smaller than 100 nm, it is possible to surely dispose the metal layer 55 at the position overlapping the overlapping part 534 even if a misalignment occurs in the forming position of the metal layer 55.

Further, by setting the projecting amount to be no larger than 3 μm, it is possible to prevent the deformation of the flexible part 412C due to an increase in the area of the metal layer 55 from being hindered, and it is possible to prevent the transmission/reception sensitivity of the ultrasonic transducer 45 from decreasing.

Here, in the plan view, the distance dimension between the outer peripheral edge 533 (the overlapping part 534) of the upper electrode 53 and the lower electrode covering 513 is, for example, 5 μm. Therefore, by setting the projecting amount to be no larger than 3 μm, it is possible to prevent the metal layer 55 from overlapping the lower electrode covering 513 in the Z direction even if the misalignment occurs in the forming position of the metal layer 55.

Functions and Advantages of First Embodiment

According to the first embodiment configured as described above, the following advantages can be obtained.

The piezoelectric film 52 has the extending part 522 extending from the piezoelectric film main body 521 so as to straddle the outer peripheral edge 533. The extending part 522 is not covered with the upper electrode 53.

Here, since the piezoelectric film main body 521 of the piezoelectric film 52 deforms when the piezoelectric element main body 50 is driven, the stress is apt to be concentrated at a position overlapping the outer peripheral edge 501 of the piezoelectric element main body 50. Since the piezoelectric film 52 is covered with the upper electrode 53 except the extending part 522, the stress is relaxed by the elasticity of the upper electrode 53. Therefore, the cracks are prevented from occurring in the piezoelectric film 52 in the edge parts on the ±X sides of the outer peripheral edge 501. In contrast, since the extending part 522 of the piezoelectric film 52 is not covered with the upper electrode 53, there is a possibility that the stress is concentrated at the position overlapping the overlapping part 534 of the piezoelectric film 52 to cause the cracks. Further, if water infiltrates the cracks, there is a possibility that the lower electrode 51 and the upper electrode 53 are shorted at the position overlapping the overlapping part 534 to thereby burn out the piezoelectric film 52.

In contrast, in the present embodiment, the insulating layer 54 and the metal layer 55 extend from the upper electrode main body 531 to the extending part 522 straddling the overlapping part 534 in the plan view. In such a configuration, due to the elasticity of the metal layer 55, it is possible to relax the stress concentration on the position overlapping the overlapping part 534 of the piezoelectric film 52. Therefore, it is possible to prevent the cracks and the burnout from occurring in the piezoelectric film 52, and it is possible to prevent the performance degradation of the piezoelectric element 5.

Further, by disposing the metal layer 55 at the position overlapping the overlapping part 534, it is possible to improve the water-resistance. Thus, it is possible to more preferably prevent the burnout of the piezoelectric film 52 in the overlapping part 534.

The metal layer 55 is formed using at least one of Pt, Ir, Ti, Zr, Au, Ni, NiCr, and TiW. In such a configuration, it is possible to provide the metal layer 55 with the elasticity capable of preventing the cracks of the piezoelectric film 52 from occurring while allowing the deformation of the piezoelectric film 52.

The insulating layer 54 is formed using at least one of $Al_2O_3$, $TaO_x$, $HfO_x$, and $SiO_2$. In such a configuration, the adhesiveness of the insulating layer 54 to the piezoelectric film 52, the upper electrode 53, and the metal layer 55 can be improved. Therefore, despite the intervention of the insulating layer 54, it is possible to make the elastic force of the metal layer 55 act on the piezoelectric film 52, and thus, it is possible to relax the stress of the piezoelectric film 52. Further, it is possible to improve the water-resistance of the insulating layer 54 compared to the case of forming the insulating layer 54 using a resin material such as an adhesive. Therefore, it is possible to more preferably prevent the burnout of the piezoelectric film 52 described above.

The Y-side end edge 551 of the metal layer 55 is located on the flexible part 412C and between the overlapping part 534 and the lower electrode covering 513 in the Y direction. In other words, the metal layer 55 extends along the Y direction to a position prior to overlapping the lower electrode covering 513. Here, it is possible to reduce the force acting in the direction of hindering the deformation of the flexible part 412C compared to the case in which the lower electrode covering 513 and the metal layer 55 overlap each other in the area where the piezoelectric film 52 overlaps the flexible part 412C. Therefore, it is possible to prevent the deformation of the flexible part 412C from being hindered, and by extension, the transmission/reception sensitivity of the ultrasonic transducer 45 from being deteriorated.

Modified Examples of First Embodiment

In the first embodiment, the insulating layer 54 is formed to cover the overlapping part 534 and the extending part 522 of the piezoelectric film 52. Further, the metal layer 55 extends from the upper electrode main body 531 toward the outside of the overlapping part 534, and is disposed at a position surrounding the overlapping part 534. However, it is sufficient for the metal layer 55 to be disposed so as to cover the overlapping part 534. Further, it is sufficient for the insulating layer 54 to be disposed at a position where the insulating layer 54 can isolate the metal layer 55 from the lower electrode 51 and the upper electrode 53.

Modified Example 1

Figure 6:
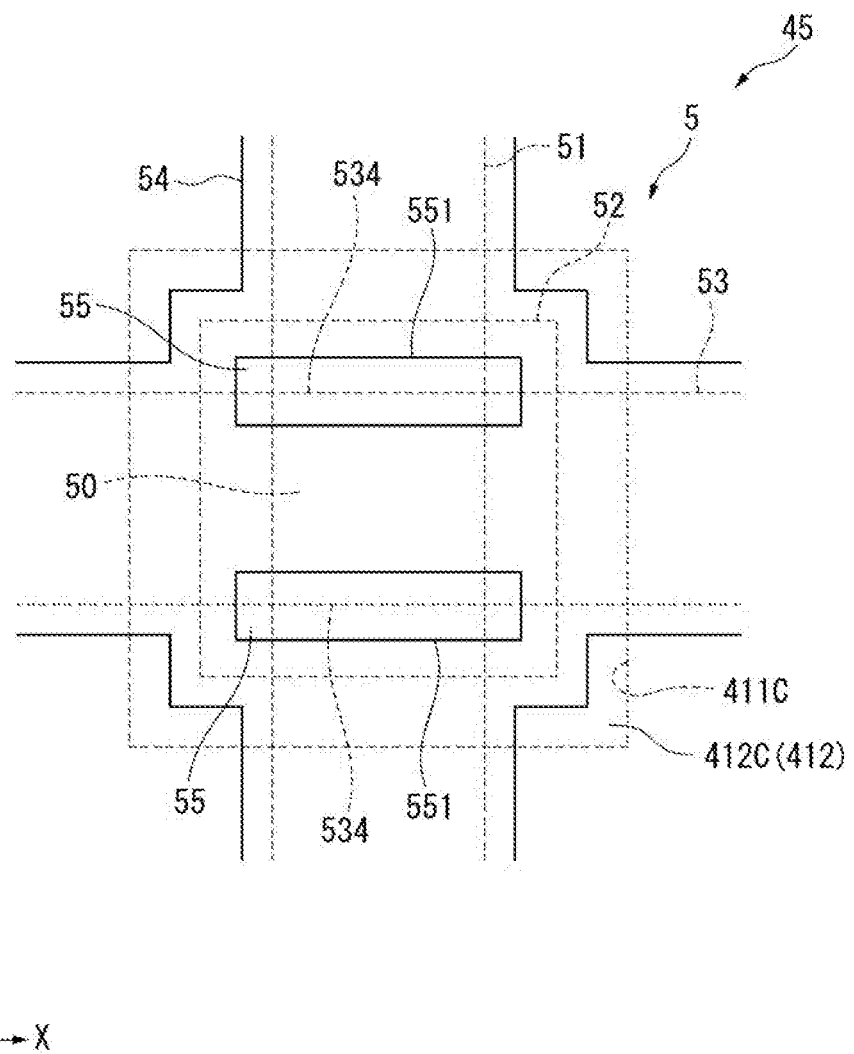
FIG. 6 is a plan view schematically showing an ultrasonic transducer according to a modified example of the first embodiment.

FIG. 6 is a plan view schematically showing an ultrasonic transducer according to a modified example of the first embodiment.

As shown in FIG. 6, it is also possible for the insulating layer 54 to be disposed so as to cover the lower electrode 51, the piezoelectric film 52, and the upper electrode 53 in the plan view in the Z direction. As described above, the insulating layer 54 has water-resistance, and can therefore prevent the deterioration of the lower electrode 51, the piezoelectric film 52, and the upper electrode 53 due to moisture.

Modified Example 2

Figure 7:
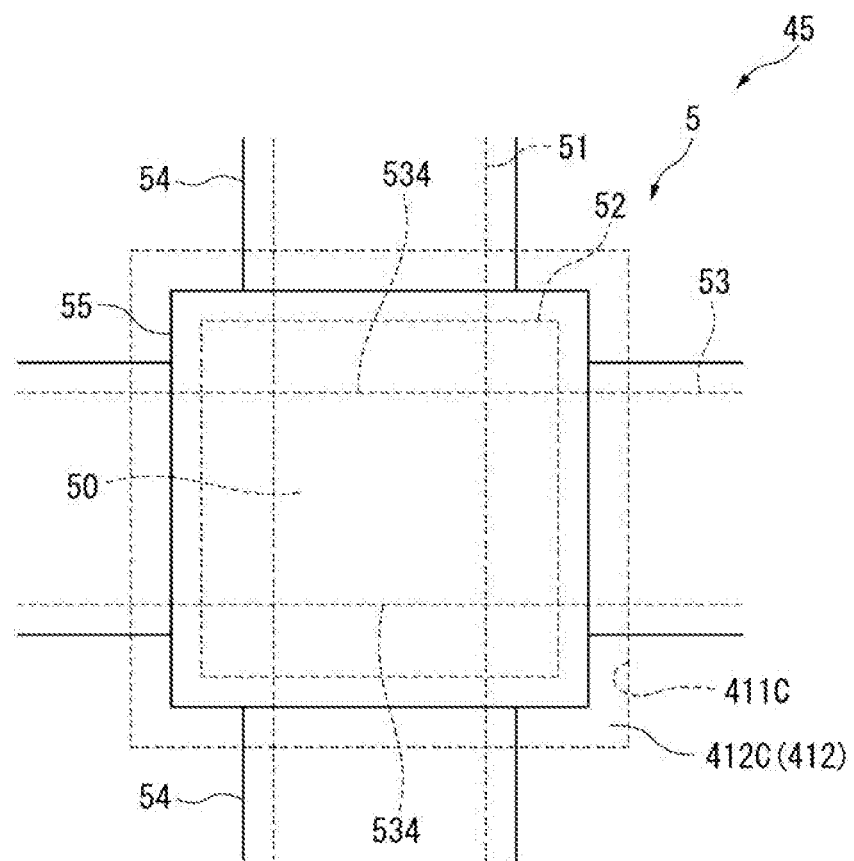
FIG. 7 is a plan view schematically showing an ultrasonic transducer according to a modified example of the first embodiment.
Figure 8:
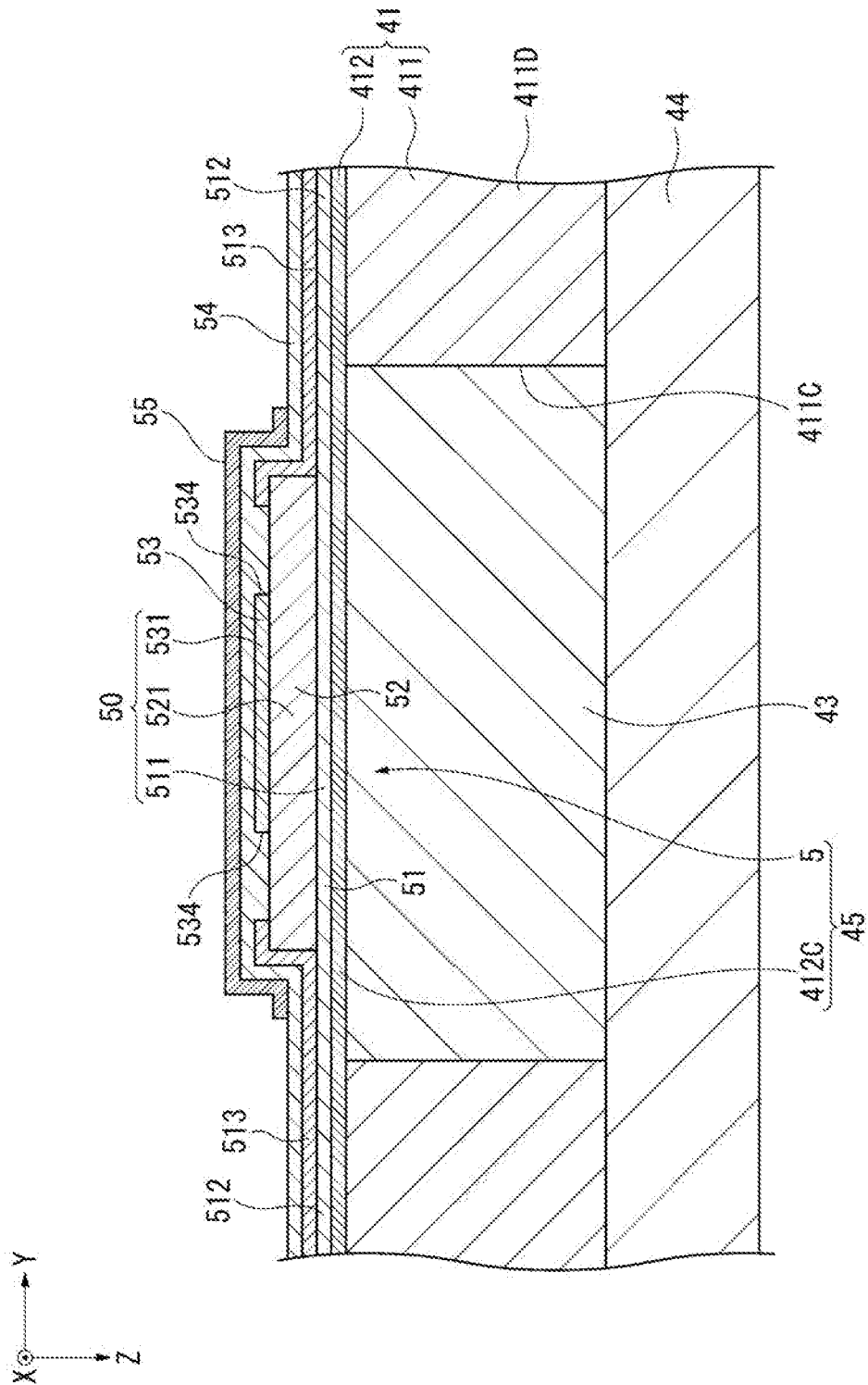
FIG. 8 is a cross-sectional view schematically showing the ultrasonic transducer according to the modified example of the first embodiment.

FIG. 7 is a plan view schematically showing an ultrasonic transducer according to a modified example of the first embodiment, and FIG. 8 is a cross-sectional view schematically showing the ultrasonic transducer according to the modified example.

As shown in FIG. 7, it is also possible for the metal layer 55 to be disposed so as to cover the entire surface of the piezoelectric film 52 in the plan view in the Z direction. In this case, as shown in FIG. 8, in the Y direction, the Y-side end edge 551 of the metal layer 55 is located on the outer side of the outer peripheral edge of the piezoelectric film 52. In other words, in Modified Example 2, since the lower electrode 51, the piezoelectric film 52, and the upper electrode 53 are covered with the metal layer 55 having water-resistance in addition to the insulating layer 54, the deterioration due to moisture is more strongly prevented.

Modified Example 3

Figure 9:
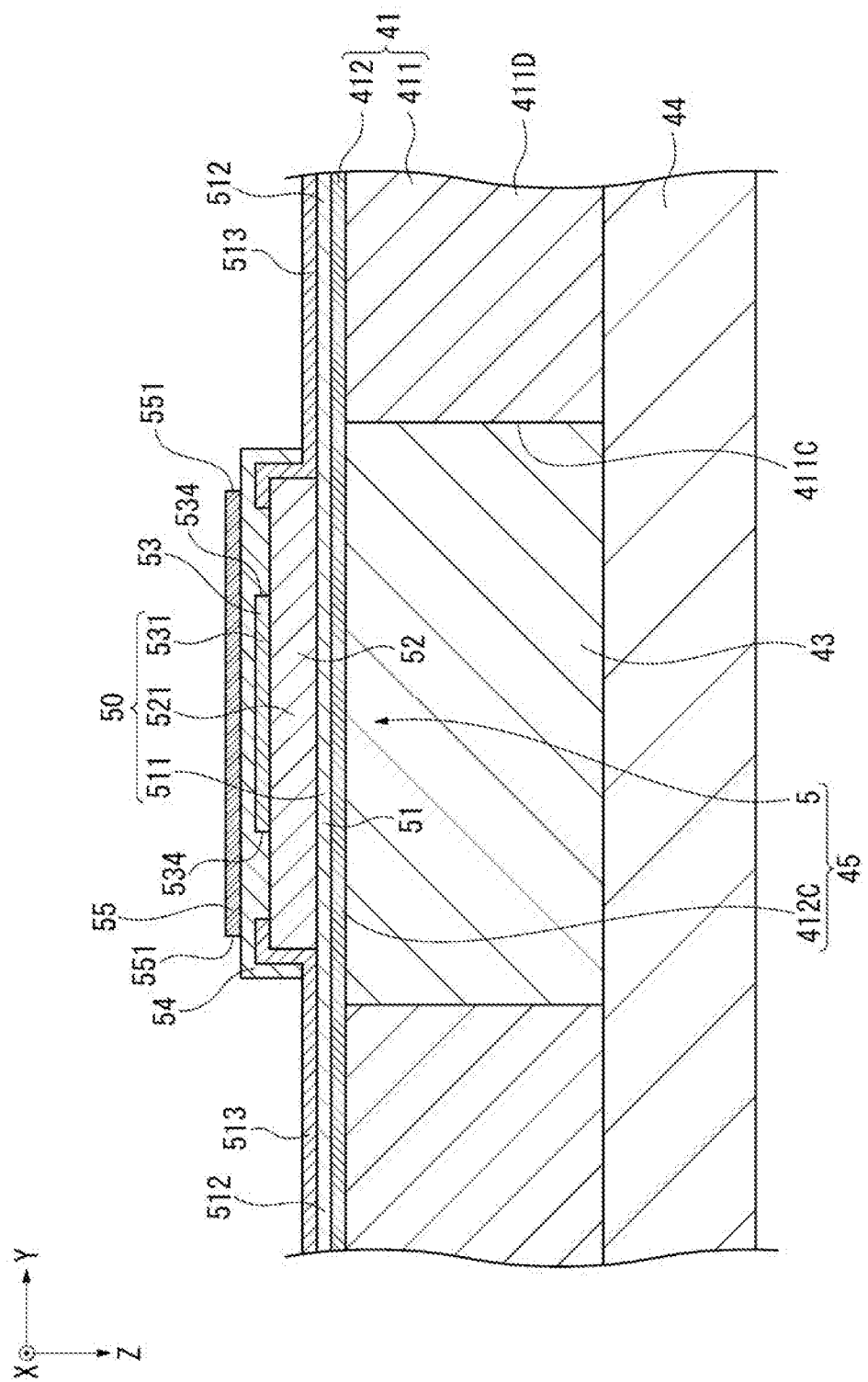
FIG. 9 is a cross-sectional view schematically showing an ultrasonic transducer according to a modified example of the first embodiment.

FIG. 9 is a cross-sectional view schematically showing an ultrasonic transducer according to a modified example of the first embodiment.

In the first embodiment, there is illustrated the configuration in which the Y-side end edge 551 of the metal layer 55 is disposed between the upper electrode main body 531 (the overlapping part 534) and the lower electrode covering 513 in the Y direction, but the configuration is not limited to the illustration. For example, as shown in FIG. 9, it is also possible for the metal layer 55 to extend to a position where the metal layer 55 overlaps the lower electrode covering 513 in the Y direction. In other words, the Y-side end edge 551 is located on the −Z side of the lower electrode covering 513. In such a configuration, similarly to Modified Example 2, the lower electrode 51, the piezoelectric film 52, and the upper electrode 53 are covered with the insulating layer 54 and the metal layer 55, and thus, the deterioration due to moisture is more strongly prevented. Further, in Modified Example 3, the area of the metal layer 55 can be reduced compared to Modified Example 2, and thus, the problem that the deformation of the piezoelectric element 5 is hindered by the metal layer 55 can more reliably be prevented from occurring.

Second Embodiment

Hereinafter, a second embodiment will be described.

In the ultrasonic transducer according to the first embodiment, the piezoelectric element main body 50 is provided to the flexible part 412C. More specifically, in the plan view in the Z direction, the piezoelectric element main body 50 is located on the inner side of the outer peripheral edge of the aperture 411C. In contrast, the second embodiment is different from the first embodiment in the point that at least a part of the piezoelectric element main body 50 is disposed on the flexible part 412C, and the overlapping part 534 is located on the outer side of the outer peripheral edge of the aperture 411C.

It should be noted that in the following description, constituents substantially the same as those of the first embodiment will be denoted by the same reference symbols, and the explanation thereof will be omitted or simplified.

Figure 10:
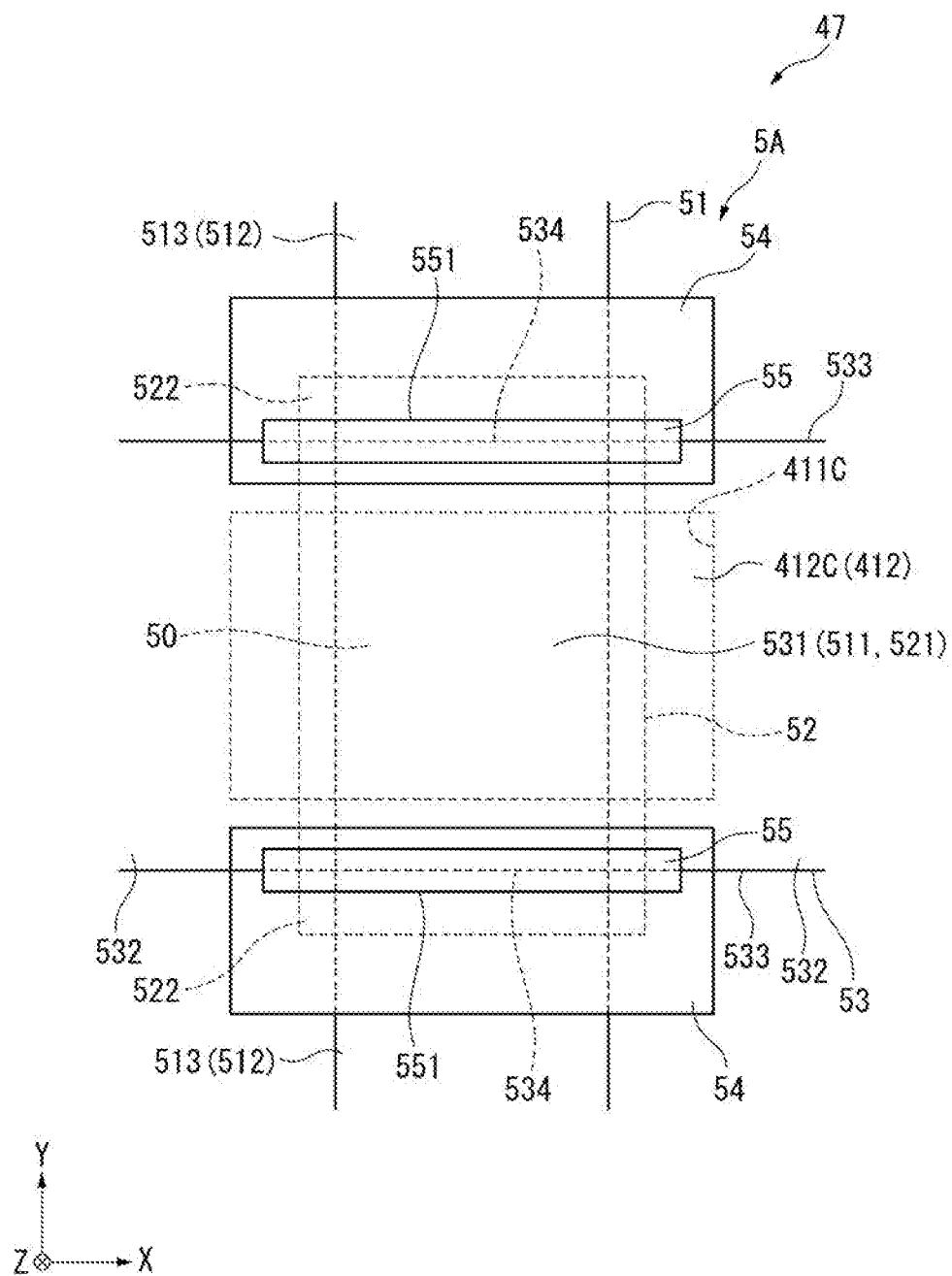
FIG. 10 is a plan view schematically showing an ultrasonic transducer according to a second embodiment of the invention.

FIG. 10 is a plan view schematically showing an ultrasonic transducer 47 according to the second embodiment. Further, FIG. 11 is a cross-sectional view of the ultrasonic transducer 47 according to the second embodiment.

As shown in FIG. 10, the ultrasonic transducer 47 is configured including a piezoelectric element 5A and the flexible part 412C. In the piezoelectric element 5A, the extending part 522 is located outside the aperture 411C in the plan view. In other words, the overlapping part 534 is located outside the aperture 411C, and overlaps the wall 411D.

Figure 11:
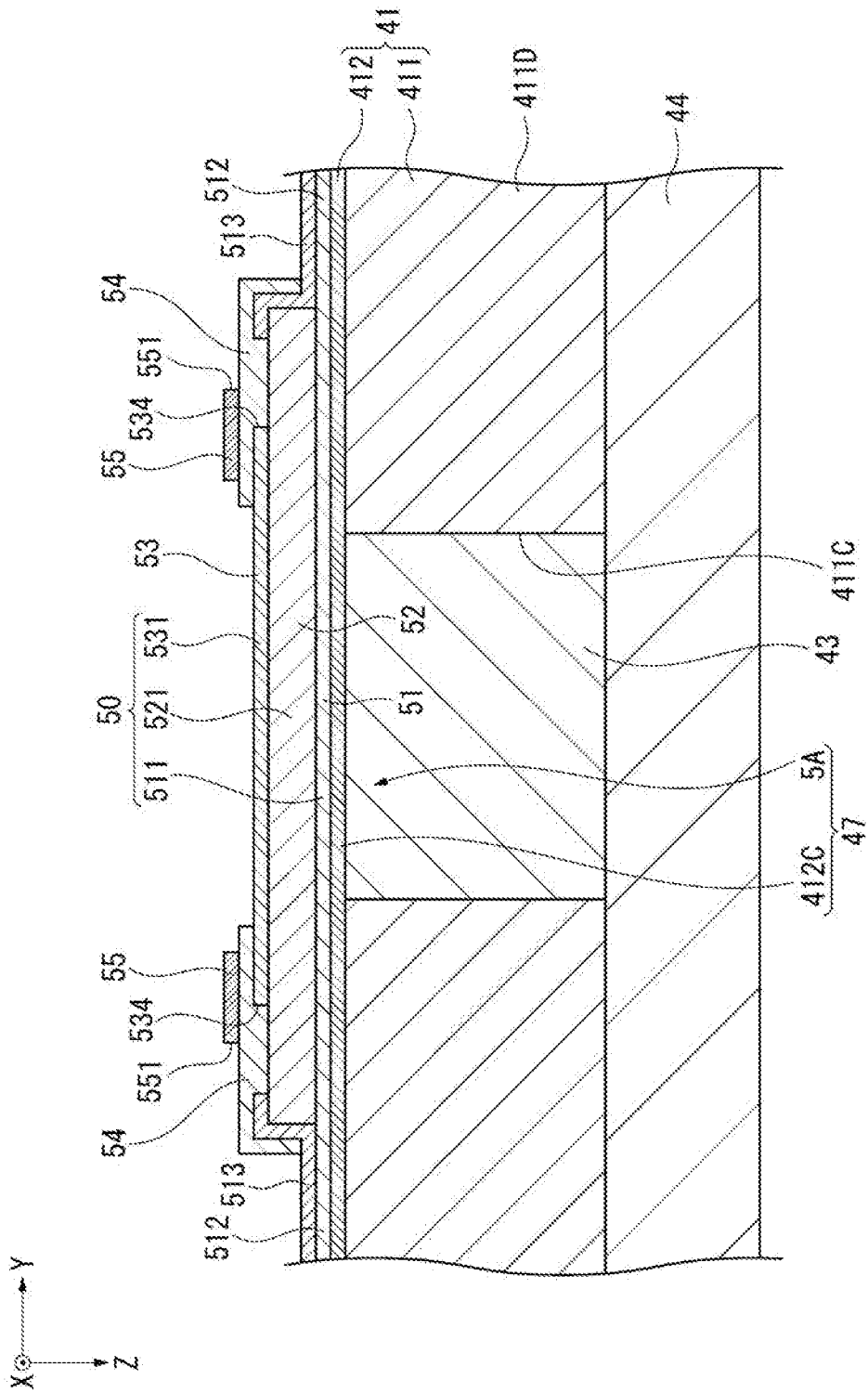
FIG. 11 is a cross-sectional view schematically showing the ultrasonic transducer according to the second embodiment.

Specifically, as shown in FIG. 10 and FIG. 11, the upper electrode 53 of the second embodiment is larger in the width dimension in the Y direction than the aperture 411C. The outer peripheral edge 533 of the upper electrode 53, namely the overlapping part 534 as the outer peripheral edge of the upper electrode main body 531, overlaps the wall 411D.

Further, the piezoelectric film 52 is similarly larger in the width dimension in the Y direction than the aperture 411C. In other words, in the present embodiment, the piezoelectric film main body 521 is large in the width dimension in the Y direction. Further, the piezoelectric film 52 extends in the Y direction straddling the overlapping part 534 on the wall 411D.

It should be noted that the lower electrode 51 and the piezoelectric film 52 are smaller in the width dimension in the X direction than the aperture 411C similarly to the first embodiment. In other words, the piezoelectric element main body 50 is smaller in the width dimension in the X direction than the aperture 411C, and is larger in the width dimension in the Y direction than the aperture 411C.

The insulating layer 54 is disposed so as to cover the overlapping part 534 of the upper electrode 53 and the extending part 522 similarly to the first embodiment.

The metal layer 55 is disposed so as to cover the overlapping part 534.

In the present embodiment, the insulating layer 54 and the metal layer 55 are disposed at a position overlapping the wall 411D in the Z direction, and are located on the outer side of the aperture 411C.

Functions and Advantages of Second Embodiment

According to the second embodiment, the following functions and advantages can be obtained in addition to substantially the same functions and advantages as in the first embodiment.

The element substrate 41 has the aperture 411C, which supports the vibrating film 412, and is blocked by the vibrating film 412. Further, a part of the piezoelectric element main body 50 is disposed on the flexible part 412C overlapping the aperture 411C of the vibrating film 412. Further, the overlapping part 534 is disposed in an area other than the flexible part 412C of the vibrating film 412, namely the position overlapping the wall 411D in the plan view. Thus, it is possible to prevent the deformation of the piezoelectric film 52 at the position overlapping the overlapping part 534, to more strongly prevent the concentration of the stress.

Here, in the case in which the insulating layer 54 and the metal layer 55 are disposed at the position overlapping the flexible part 412C in the plan view, there is a possibility that the deformation of the piezoelectric element main body 50 and the vibrating film 412 in the stacking direction is hindered by the insulating layer 54 and the metal layer 55, and thus, the transmission/reception sensitivity of the ultrasonic transducer is degraded. In contrast, in the present embodiment, the insulating layer 54 and the metal layer 55 are located outside the aperture 411C in the plan view. Therefore, it is possible to prevent the deformation of the piezoelectric element main body 50 and the vibrating film 412 in the stacking direction from being hindered, and thus, it is possible to prevent the degradation of the transmission/reception sensitivity of the ultrasonic transducer 47.

Further, the piezoelectric element main body 50 is smaller in dimension in the X direction than the aperture 411C. In other words, a part of the outer peripheral edge 501 of the piezoelectric element main body 50 is located inside the aperture 411C. In such a configuration, it is possible to increase the area of a part in which the piezoelectric element main body 50 can be deformed in the stacking direction to increase the output of the ultrasonic transducer 47 compared to the case in which the whole of the outer peripheral edge 501 of the piezoelectric element main body 50 is located outside the aperture 411C.

Modified Example of Second Embodiment

Figure 12:
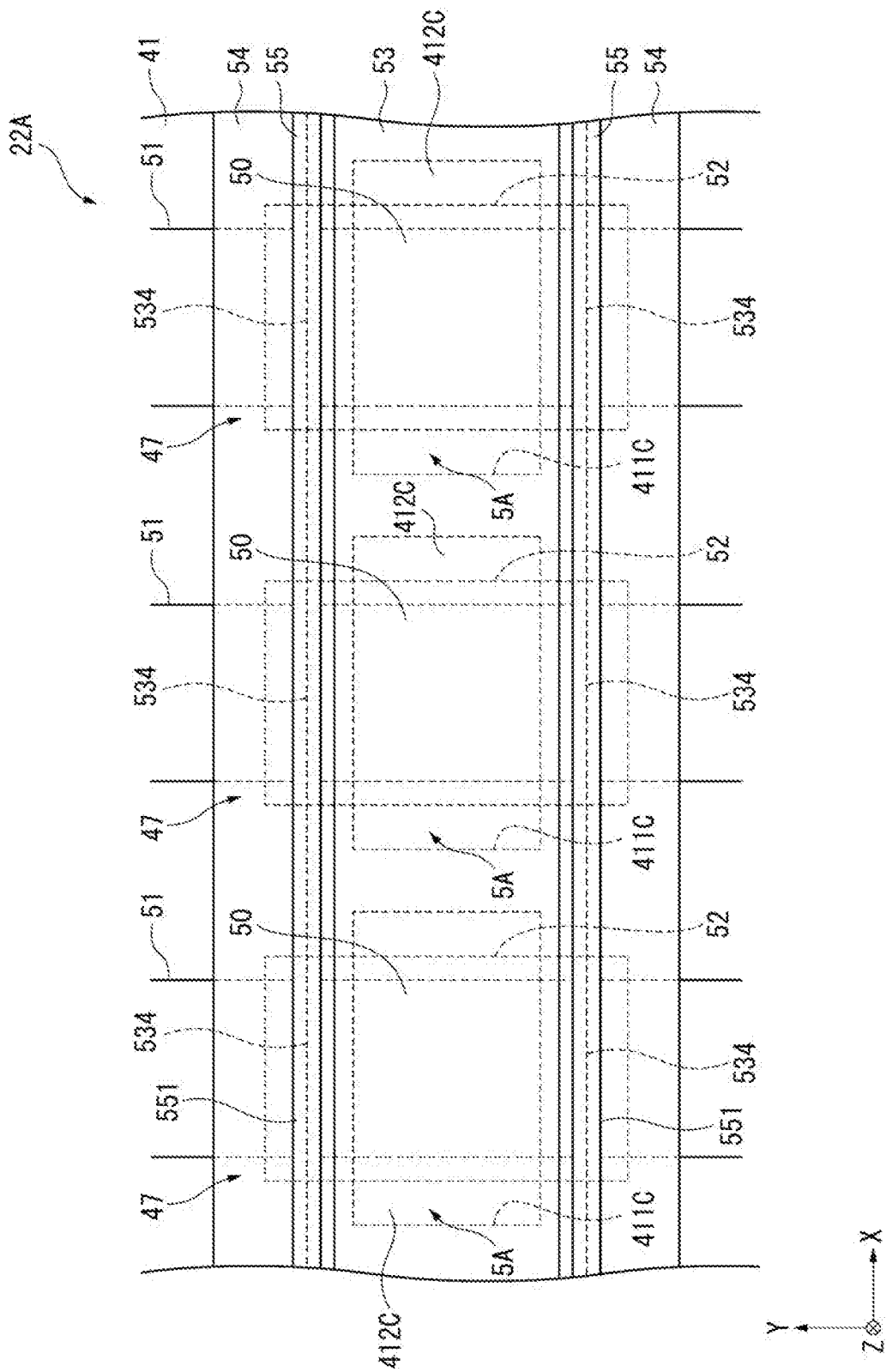
FIG. 12 is a plan view schematically showing an ultrasonic device according to a modified example of the second embodiment.

FIG. 12 is a plan view schematically showing the element substrate 41 in an ultrasonic device 22A according to a modified example the second embodiment.

In the second embodiment, the insulating layer 54 and metal layer 55 are individually provided to the ultrasonic transducers 47, but the invention is not limited to this configuration, and it is also possible for the insulating layer 54 and the metal layer 55 to be formed over a plurality of ultrasonic transducers 47.

As shown in FIG. 12, the insulating layer 54 and the metal layer 55 of the ultrasonic device 22A are formed at a position covering the outer peripheral edge 533 of the upper electrode 53 along the X direction. In other words, the insulating layer 54 and the metal layer 55 are formed so as to straddle the plurality of ultrasonic transducers 47 disposed along the X direction.

In such a configuration, there is no need to dispose the insulating layer 54 and the metal layer 55 individually to each of the ultrasonic transducers 47, and it is possible to simplify the shapes of the insulating layer 54 and the metal layer 55. For example, patterning of the insulating layer 54 and the metal layer 55 is easy, and the formation of the insulating layer 54 and the metal layer 55 is easy.

Further, since the insulating layer 54 and the metal layer 55 cover the outer peripheral edge 533 of the upper electrode 53, exfoliation of the upper electrode 53 can preferably be prevented.

It should be noted that the insulating layer 54 and the metal layer 55 can also be formed on the entire surface except the positions overlapping the apertures 411C. In such a configuration, deterioration of the lower electrode 51 and the upper electrode 53 can be prevented. Further, even in such a configuration, the insulating layer 54 and the metal layer 55 are not disposed at the position overlapping the aperture 411C, it is possible to prevent the deformation of the flexible part 412C from being hindered.

Further, in the second embodiment described above, there is illustrated the configuration in which the dimension of the piezoelectric element main body 50 in the X direction is smaller than that of the aperture 411C, but the invention is not limited to this configuration. For example, the dimension of the piezoelectric element main body 50 in the X direction can also be larger than that of the aperture 411C. In other words, it is also possible to adopt a configuration in which the whole of the outer peripheral edge 501 of the piezoelectric element main body 50 is located outside the aperture 411C.

Further, although in the second embodiment described above, it is assumed that the insulating layer 54 is located outside the aperture 411C in the plan view, it is also possible for a part of the insulating layer 54 to overlap the aperture 411C. Further, similarly, although it is assumed that the metal layer 55 is located outside the aperture 411C in the plan view, it is also possible for a part of the metal layer 55 to overlap the aperture 411C.

Third Embodiment

Hereinafter, a third embodiment will be described.

In the first embodiment, there is illustrated the ultrasonic measurement device 1 equipped with the piezoelectric element 5. In contrast, in the third embodiment, there are described a liquid jet head and a liquid jet device each equipped with the piezoelectric element 5.

Figure 13:
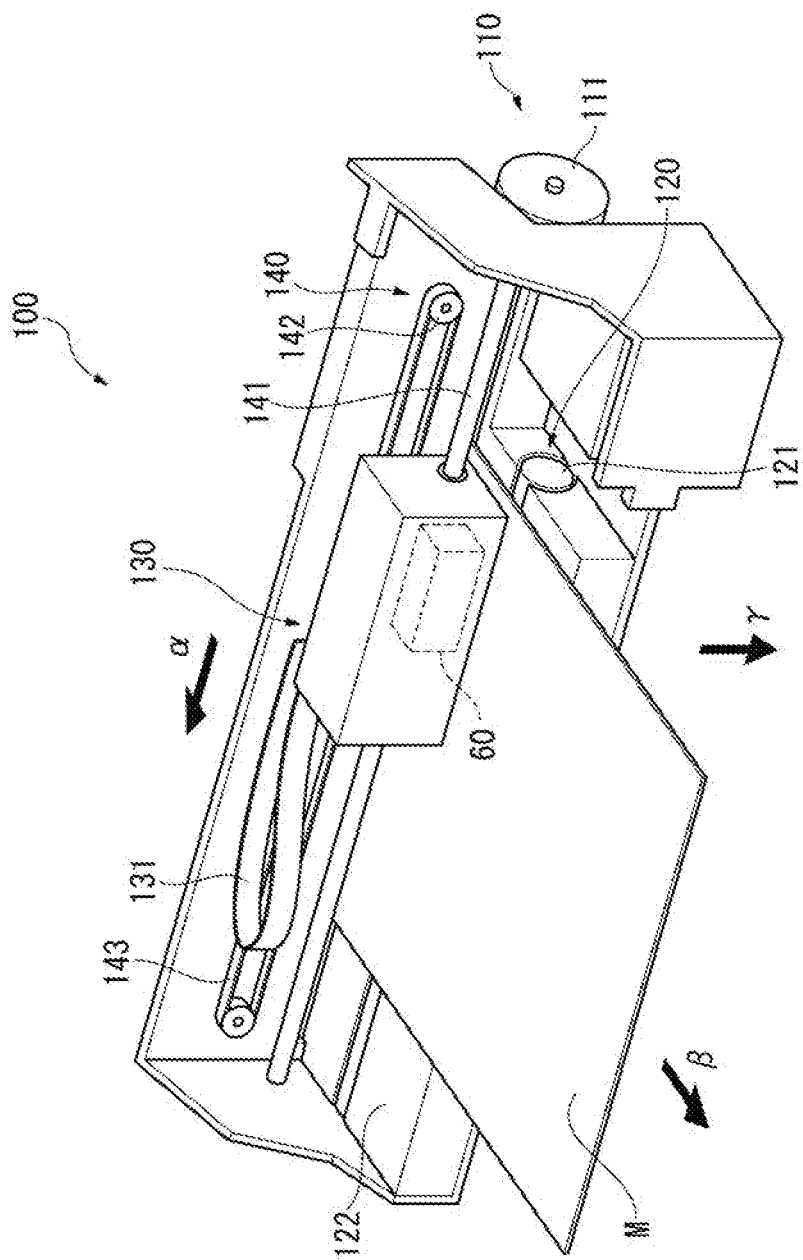
FIG. 13 is a diagram showing a schematic configuration of a printer according to a third embodiment of the invention.

FIG. 13 is a diagram showing a configuration example of an appearance of a printer 100 according to the present embodiment.

The printer 100 corresponds to the liquid jet device, and is provided with a supply unit 110 for supplying a medium, a conveying unit 120 for conveying the medium, a carriage 130 attached with a recording head 60, a carriage moving unit 140 for moving the carriage 130, and a control unit (not shown) for controlling the printer 100 as shown in FIG. 13.

The printer 100 controls the units 110, 120, and 140 and the carriage 130 based on print data input from an external device such as a personal computer to print an image on the medium M.

The supply unit 110 supplies the medium M at an image forming position. For example, the supply unit 110 is provided with a roll body 111 around which the medium M is wound, a roll driving motor (not shown), a roll driving gear train (not shown), and so on. Further, based on the command from the control unit, the roll driving motor is rotationally driven, and the rotational force of the roll driving motor is transmitted to the roll body 111 via the roll driving gear train. Thus, the roll body 111 rotates, and a paper sheet wound around the roll body 111 is supplied on the downstream side (β side) in the β direction (a sub-scanning direction).

The conveying unit 120 conveys the medium M supplied from the supply unit 110 along the β direction. For example, the conveying unit 120 is provided with a conveying roller 121, a driven roller (not shown) disposed across the medium M from the conveying roller 121, and driven by the conveying roller 121, and a platen 122 disposed on the downstream side in the β direction of the conveying roller 121. The driving force from the roll driving motor not shown is transmitted to the conveying roller 121, and when the roll driving motor is driven by the control of the control unit (not shown), the conveying roller 121 is rotationally driven by the rotational force, and the conveying roller 121 conveys the medium M along the β direction in the state of sandwiching the medium M between the driven roller and the conveying roller 121.

The carriage 130 is attached with the recording head 60 for printing the image on the medium M. The recording head 60 is connected to the control unit via a cable 131. The recording head 60 will be described later. The carriage 130 is disposed so as to be movable along an α direction (a main scanning direction) crossing the β direction due to the carriage moving unit 140.

The carriage moving unit 140 reciprocates the carriage 130 along the α direction. For example, the carriage moving unit 140 is provided with a carriage guide shaft 141, a carriage motor 142, and a timing belt 143. The carriage guide shaft 141 is disposed along the α direction, and the both ends of the carriage guide shaft 141 are fixed to the housing of the printer 100. The carriage motor 142 drives the timing belt 143. The timing belt 143 is supported roughly in parallel to the carriage guide shaft 141, and a part of the carriage 130 is fixed to the timing belt 143. When the carriage motor 142 is driven based on the command of the control unit, the timing belt 143 is made to run forward and backward, and the carriage 130 fixed to the timing belt 143 reciprocates while being guided by the carriage guide shaft 141.

Figure 14:
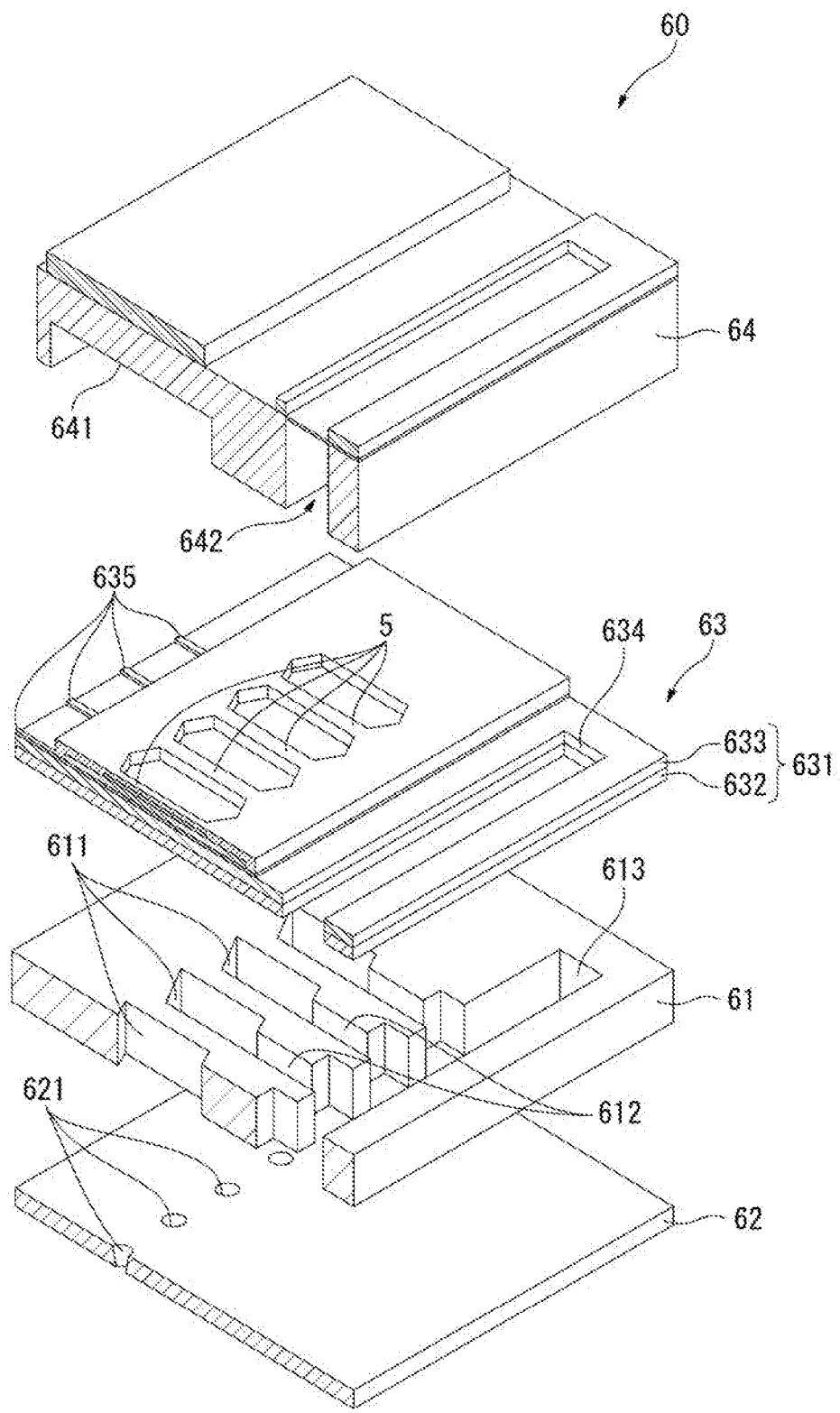
FIG. 14 is an exploded perspective view schematically showing a recording head according to the third embodiment.

FIG. 14 is an exploded perspective view schematically showing the recording head 60.

The recording head 60 corresponds to the liquid jet head, and ejects the ink supplied from an ink tank (not shown) toward a γ direction crossing the α direction and the β direction to form the image on the medium M. As shown in FIG. 14, the recording head 60 is provided with a pressure chamber forming substrate 61, a nozzle plate 62, an actuator unit 63, and a sealing plate 64.

The pressure chamber forming substrate 61 is a plate member formed of, for example, a silicon single-crystal substrate. The pressure chamber forming substrate 61 is provided with a plurality of pressure chambers 611, ink supply channels 612 for supplying each pressure chamber 611 with ink, and a communication part 613 communicated with each of the pressure chambers 611 via the respective ink supply channels 612.

The plurality of pressure chambers 611 is disposed so as to correspond one-to-one to the nozzles 621 constituting a nozzle row provided to the nozzle plate 62 as described later. Specifically, the pressure chambers 611 are formed along the nozzle row direction at the same pitch as the forming pitch of the nozzles 621.

The communication part 613 is formed along the plurality of pressure chambers 611. The communication part 613 communicates with a communication aperture 634 of the vibrating plate 631 and a liquid chamber space part 642 of the sealing plate 64, and is filled with the ink supplied from the ink tank (not shown). The ink with which the communication part 613 is filled is supplied to the pressure chambers 611 via the ink supply channels 612. In other words, the communication part 613 constitutes a reservoir (a common liquid chamber) as an ink chamber common to the pressure chambers 611.

It should be noted that the ink supply channels 612 are each formed to have a width narrower than that of the pressure chamber 611 to provide a flow pass resistance with respect to the ink flowing from the communication part 613 into the pressure chamber 611.

The nozzle plate 62 is provided with the nozzle row constituted by the plurality of nozzles 621, and is bonded to one surface (a surface on the opposite side to the actuator unit 63) of the pressure chamber forming substrate 61. The plurality of nozzles 621 is formed at the pitch corresponding to the dot forming density (e.g., 300 dpi). It should be noted that the nozzle plate 62 is formed of, for example, glass ceramics, a silicon single-crystal substrate, or stainless steel.

The actuator unit 63 is configured including the vibrating plate 631 disposed on the opposite side to the nozzle plate 62 of the pressure chamber forming substrate 61, and the piezoelectric element 5 stacked on the vibrating plate 631.

The vibrating plate 631 includes an elastic film 632 formed on the pressure chamber forming substrate 61, and an insulator film 633 formed on the elastic film 632. It should be noted that as the elastic film 632, there is preferably used, for example, silicon dioxide ($SiO_2$) having the thickness of 300 through 2000 nm. Further, as the insulator film 633, there is preferably used, for example, zirconium oxide ($ZrO_x$) having the thickness of 30 through 600 nm. The area for blocking the pressure camber 611 of the vibrating plate 631 is an area (a flexible part) allowed to make a distortional deformation in the direction of coming closer to and getting away from the nozzle 621 due to the drive of the piezoelectric element 5. It should be noted that the part corresponding to the communication part 613 of the pressure chamber forming substrate 61 in the vibrating plate 631 is provided with a communication aperture 634 communicated with the communication part 613.

As described above, the piezoelectric element 5 is provided with the piezoelectric element main body 50, the insulating layer 54, and the metal layer 55, and the piezoelectric element main body 50 is configured as the laminated body having the lower electrode 51, the piezoelectric film 52, and the upper electrode 53 stacked in sequence. The piezoelectric element 5 is disposed at the position corresponding to the pressure chamber 611 to constitute the piezoelectric actuator together with the flexible part as the area blocking the pressure chamber 611 of the vibrating plate 631. It should be noted that although not shown in the drawings, the lower electrode 51 and the upper electrode 53 are connected to the electrode terminals formed in the terminal area using lead electrodes 635.

Here, although in FIG. 14 the configuration of the piezoelectric element 5 is illustrated in a simplified manner, the metal layer 55 is also disposed at the position overlapping the overlapping part 534 in the plan view viewed from the thickness direction of the vibrating plate 631 in the present embodiment. It should be noted that similarly to the piezoelectric element 5 according to the second embodiment shown in FIG. 11, it is preferable that the overlapping part 534 is located on the outer side of the pressure chamber 611 in the plan view, and the metal layer 55 is disposed, but the invention is not limited to this configuration. Specifically, similarly to the first embodiment, it is possible for the overlapping part 534 and the metal layer 55 to be located at the position overlapping the pressure chamber 611 in the plan view.

The sealing plate 64 is bonded to the surface on the opposite side to the pressure chamber forming substrate 61 of the actuator unit 63. On the surface located on the actuator unit 63 side of the sealing plate 64, there is formed a housing space part 641 capable of housing the piezoelectric elements 5. Further, in an area corresponding to the communication aperture 634 and the communication part 613 of the sealing plate 64, there is disposed the liquid chamber space part 642. The liquid chamber space part 642 is communicated with the communication aperture 634 and the communication part 613 to constitute the reservoir functioning as the ink chamber common to the pressure chambers 611. It should be noted that although not shown in the drawings, the sealing plate 64 is provided with a wiring aperture penetrating in the thickness direction at a position corresponding to the terminal area of the actuator unit 63. In the wiring aperture, there are exposed the electrode terminals in the terminal area described above. These electrode terminals are connected to wiring members not shown connected to the printer main body.

In the recording head 60 having such a configuration, the ink is introduced from an ink cartridge to fill the reservoir, the ink supply channels 612, the pressure chambers 611, and the flow channels to the nozzles 621 with the ink. Then, when the piezoelectric elements 5 corresponding respectively to the pressure chambers 611 are driven due to the supply of the drive signal from the printer main body, the areas (the flexible parts) corresponding to the pressure chambers 611 of the vibrating plate 631 are displaced to cause pressure variations in the respective pressure chambers 611. By controlling the pressure variations, the ink is ejected from the respective nozzles 621.

Functions and Advantages of Third Embodiment

In the third embodiment configured as described above, the piezoelectric elements 5 are each provided with the insulating layer 54 and the metal layer 55 extending from the upper electrode main body 531 to the extending part 522 so as to straddle the overlapping part 534 in the plan view similarly to the first embodiment. In such a configuration, due to the elasticity of the metal layer 55, it is possible to relax the stress concentration on the position overlapping the overlapping part 534 of the piezoelectric film 52. Therefore, it is possible to prevent the cracks and the burnout from occurring in the piezoelectric film 52, and it is possible to prevent the performance degradation of the piezoelectric element 5, and by extension, it is possible to prevent the performance degradation of the recording head 60.

Other Modified Examples

It should be noted that the invention is not limited to the embodiments and the modified examples described above, but includes modifications and improvements within a range where the advantages of the invention can be achieved, and configurations, which can be obtained by, for example, arbitrarily combining the embodiments.

In each of the embodiments described above, the piezoelectric film 52 is disposed so as to overlap the entire range of the overlapping part 534, but the invention is not limited to this configuration. For example, it is also possible for the piezoelectric film 52 to be disposed so as to extend from the inside of at least a part of the overlapping part 534 toward the outside of the overlapping part 534. Even in such a configuration, by forming the metal layer 55 at the position covering at least a part of the overlapping part 534, it is possible to prevent the cracks and the burnout from occurring in the piezoelectric film 52.

In each of the embodiments described above, the lower electrode main body 511 and the upper electrode main body 531 are each constituted by a single conductive layer formed of a metal material, but the invention is not limited to this configuration. It is also possible to adopt a configuration having two or more conductive layers, or it is also possible to form the lower electrode main body 511 and the upper electrode main body 531 with a conductive material other than metal. Further, similarly, the piezoelectric film 52 can also be formed of two or more piezoelectric layers. Further, similarly, the metal layer 55 can also be formed of two or more metal layers.

In each of the embodiments described above, there is illustrated the configuration in which the piezoelectric element 5 and the sealing plate 42 are disposed on the opposite side to the substrate main body 411 (the aperture 411C) of the vibrating film 412, the acoustic layer 43 and the acoustic lens are provided to the substrate main body 411, and the transmission and the reception of the ultrasonic wave are performed through the surface on the substrate main body 411 side, but the invention is not limited to this configuration. For example, the piezoelectric element 5, the acoustic layer 43 and the acoustic lens 44 are provided on the opposite side to the substrate main body 411 of the vibrating film 412, the sealing plate 42 (a reinforcing plate) is provided to the substrate main body 411, and the transmission and the reception of the ultrasonic wave are performed through the surface on the opposite side to the substrate main body 411.

In each of the embodiments described above, the ultrasonic transducer 45 provided with the flexible part 412C corresponding to the drive section, and the piezoelectric element 5 for vibrating the flexible part 412C is illustrated as an example of the piezoelectric actuator, but the invention is not limited to this configuration. For example, the piezoelectric actuator can also be provided with a drive section other than the vibrating film. The piezoelectric element according to the invention can preferably be applied to, for example, the mirror device provided with a reflecting film as the drive section and for driving the piezoelectric element to thereby change the orientation and the curvature of the reflecting film.

Although in each of the embodiments described above, the ultrasonic device and the liquid jet device taking a part of a living body as the measurement object are illustrated as the electronic apparatus, the invention is not limited to these examples. For example, the configurations of the embodiments and the modified examples described above can be applied to a measurement apparatus taking a variety of types of structures as the measurement object, and performing the detection of the defects and inspection of aging of the structures. Further, the same applies to a measurement apparatus taking, for example, a semiconductor package or a wafer as the measurement object, and detecting the defects of the measurement object.

Besides the above, specific structures to be adopted when implementing the invention can be configured by arbitrarily combining the embodiments and the modified examples described above with each other, or can arbitrarily be replaced with other structures within the range in which the advantages of the invention can be achieved.

The entire disclosure of Japanese Patent Application No. 2016-191743 filed Sep. 29, 2016 is expressly incorporated herein by reference.

What is claimed is:

1. A piezoelectric element comprising:
a piezoelectric element main body having a first electrode layer, a piezoelectric layer disposed on the first electrode layer, and a second electrode layer disposed on the piezoelectric layer; and
a metal layer disposed on the second electrode layer via an insulating layer such that an entirety of the metal layer is spaced apart from the second electrode,
wherein the piezoelectric layer has an extending part extending from the piezoelectric element main body beyond an outer peripheral edge of the second electrode layer in a plan view,
the metal layer extends outward from the outer peripheral edge of the second electrode such that metal layer overlaps the extending part of the piezoelectric layer in the plan view.

2. The piezoelectric element according to claim 1, wherein
the metal layer is formed of at least one of Pt, Ir, Ti, Zr, Au, Ni, NiCr, and TiW.

3. The piezoelectric element according to claim 1, wherein
the insulating layer is formed of at least one of $Al_2O_3$, $TaO_x$, $HfO_x$, and $SiO_2$.

4. An electronic apparatus comprising:
a piezoelectric element main body having a first electrode layer, a piezoelectric layer disposed on the first electrode layer, and a second electrode layer disposed on the piezoelectric layer;
a metal layer disposed on the second electrode layer via an insulating layer such that an entirety of the metal layer is spaced apart from the second electrode;
a driver driven by the piezoelectric element main body; and
a controller configured to control the piezoelectric element main body,
wherein the piezoelectric layer has an extending part extending from the piezoelectric element main body beyond an outer peripheral edge of the second electrode layer in a plan view,
the metal layer extends outward from the outer peripheral edge of the second electrode such that metal layer overlaps the extending part of the piezoelectric layer in the plan view.

5. A piezoelectric element comprising:
a piezoelectric element main body having:
a first electrode layer;
a second electrode layer crossing the first electrode layer; and
a piezoelectric layer sandwiched between the first and second electrode layers,
an insulating layer disposed on the second electrode layer; and
a metal layer disposed on the insulating layer such that an entirety of the metal layer is spaced apart from the second electrode,
wherein the piezoelectric layer extends beyond a peripheral edge of the second electrode layer in a plan view,
in the plan view, the metal layer and the insulating layer extend outward from the peripheral edge of the second electrode to overlap the peripheral edge of the second electrode layer and the piezoelectric layer that extends beyond the peripheral edge of the second electrode.

6. The piezoelectric element according to claim 5, wherein
the metal layer is formed of at least one of Pt, Ir, Ti, Zr, Au, Ni, NiCr, and TiW.

7. The piezoelectric element according to claim 5, wherein
the insulating layer is formed of at least one of $Al_2O_3$, $TaO_x$, $HfO_x$, and $SiO_2$.

8. The piezoelectric element according to claim 5, further comprising:
a second metal layer disposed on the insulating layer,
wherein the piezoelectric layer extends beyond a second peripheral edge of the second electrode layer in the plan view, and
in the plan view, the second metal layer and the insulating layer straddle the second peripheral edge of the second electrode layer.

9. The piezoelectric element according to claim 5, further comprising:
a second insulating layer disposed on the second electrode layer; and
a second metal layer disposed on the second insulating layer,
wherein the piezoelectric layer extends beyond a second peripheral edge of the second electrode layer in the plan view, and
in the plan view, the second metal layer and the second insulating layer straddle the second peripheral edge of the second electrode layer.

10. The piezoelectric element according to claim 1, wherein the first electrode connector extends from a side of the first electrode main body in a first direction.

11. The piezoelectric element according to claim 10, wherein the second electrode layer includes a second electrode main body, and a second electrode connector connected to the second electrode main body, and
the second electrode main body overlaps the first electrode layer and the piezoelectric layer.

12. The piezoelectric element according to claim 11, wherein the second electrode connector extends from a side of the second electrode main body in a second direction that intersects with the first direction.

13. The piezoelectric element according to claim 12, wherein a width of the metal layer is larger than a width of the first electrode main body in the second direction.

* * * * *